United States Patent
Bor et al.

(10) Patent No.: US 9,603,519 B2
(45) Date of Patent: Mar. 28, 2017

(54) OPHTHALMIC RANGE FINDING

(75) Inventors: Zsolt Bor, San Clemente, CA (US); John Tamkin, San Marino, CA (US)

(73) Assignee: AMO DEVELOPMENT, LLC, Santa Ana, CA (US)

(*) Notice: Subject to any disclaimer, the term of this patent is extended or adjusted under 35 U.S.C. 154(b) by 414 days.

(21) Appl. No.: 13/531,411

(22) Filed: Jun. 22, 2012
(Under 37 CFR 1.47)

(65) Prior Publication Data

US 2013/0150836 A1    Jun. 13, 2013

Related U.S. Application Data

(60) Provisional application No. 61/637,644, filed on Apr. 24, 2012, provisional application No. 61/500,596, filed on Jun. 23, 2011.

(51) Int. Cl.
*A61F 9/008* (2006.01)
*A61B 3/14* (2006.01)
(Continued)

(52) U.S. Cl.
CPC ............... *A61B 3/14* (2013.01); *A61B 3/10* (2013.01); *A61B 3/1225* (2013.01); *A61F 9/008* (2013.01);
(Continued)

(58) Field of Classification Search
CPC A61B 3/10; A61B 3/14; A61B 3/1225; A61F 2009/00844; A61F 2009/0087;
(Continued)

(56) References Cited

U.S. PATENT DOCUMENTS

| 4,665,913 A | 5/1987 | L'Esperance, Jr. |
| 4,764,930 A | 8/1988 | Bille et al. |

(Continued)

FOREIGN PATENT DOCUMENTS

| WO | WO 2007084694 A2 * | 7/2007 |
| WO | 2007143111 A2 | 12/2007 |

(Continued)

OTHER PUBLICATIONS

International Search Report and Written Opinion for Application No. PCT/US2012/043808, mailed on Nov. 21, 2012, 14 pages.
(Continued)

*Primary Examiner* — Gary Jackson
*Assistant Examiner* — Boniface N Nganga
(74) *Attorney, Agent, or Firm* — Abbott Medical Optics Inc.

(57) ABSTRACT

Embodiments of the invention provide methods and systems for analyzing the ophthalmic anatomy of a patient posterior to the cornea. The method may include scanning a focus of a femtosecond laser beam along a path within the patient's eye. A portion of the path may be disposed posterior to the patient's cornea. The method may also include acquiring a first reflectance image and a second reflectance image associated with the focus disposed respectively at a first location of the path and a second location of the path. The method may further include determining the presence or absence of an ophthalmic anatomical feature of the eye based on a comparison between the first reflectance image and the second reflectance image.

8 Claims, 16 Drawing Sheets

(51) Int. Cl.
*A61B 3/10* (2006.01)
*A61B 3/12* (2006.01)

(52) U.S. Cl.
CPC .. *A61F 9/00831* (2013.01); *A61F 2009/0087* (2013.01); *A61F 2009/00844* (2013.01); *A61F 2009/00878* (2013.01); *A61F 2009/00889* (2013.01)

(58) Field of Classification Search
CPC .. A61F 2009/00878; A61F 2009/00889; A61F 9/008; A61F 9/0831
USPC .......................... 606/4–6; 351/205, 206, 246
See application file for complete search history.

(56) References Cited

U.S. PATENT DOCUMENTS

| | | | |
|---|---|---|---|
| 5,683,379 | A | 11/1997 | Hohla |
| 5,807,379 | A | 9/1998 | L'Esperance, Jr. |
| 5,993,438 | A | 11/1999 | Juhasz et al. |
| 6,004,313 | A | 12/1999 | Shimmick et al. |
| 6,095,651 | A | 8/2000 | Williams et al. |
| 6,203,539 | B1 | 3/2001 | Shimmick et al. |
| 6,271,915 | B1 | 8/2001 | Frey et al. |
| 6,315,413 | B1 | 11/2001 | Shimmick et al. |
| 6,331,177 | B1 | 12/2001 | Munnerlyn et al. |
| RE37,585 | E | 3/2002 | Mourou et al. |
| 2004/0070761 | A1* | 4/2004 | Horvath et al. ............. 356/399 |
| 2004/0102765 | A1* | 5/2004 | Koenig ............................. 606/5 |
| 2004/0243111 | A1 | 12/2004 | Bendett et al. |
| 2006/0106371 | A1* | 5/2006 | Muhlhoff et al. ................ 606/5 |
| 2006/0217691 | A1* | 9/2006 | Schuele et al. ................ 606/12 |
| 2007/0050165 | A1* | 3/2007 | Gray et al. .................... 702/108 |
| 2007/0185475 | A1* | 8/2007 | Frey et al. ........................ 606/4 |
| 2008/0009840 | A1* | 1/2008 | Chernyak ......................... 606/5 |
| 2008/0177256 | A1* | 7/2008 | Loesel et al. .................... 606/4 |
| 2009/0171325 | A1* | 7/2009 | Koenig .............................. 606/5 |
| 2009/0247997 | A1* | 10/2009 | Watanabe et al. ................ 606/4 |
| 2009/0247998 | A1 | 10/2009 | Watanabe et al. |
| 2009/0275929 | A1* | 11/2009 | Zickler .............................. 606/5 |
| 2010/0004641 | A1* | 1/2010 | Frey et al. ........................ 606/4 |
| 2010/0130966 | A1* | 5/2010 | Brownell .......................... 606/4 |
| 2011/0013141 | A1* | 1/2011 | Holladay et al. ............. 351/221 |
| 2011/0022036 | A1* | 1/2011 | Frey et al. ........................ 606/4 |
| 2011/0028948 | A1 | 2/2011 | Raksi et al. |
| 2011/0028949 | A1 | 2/2011 | Raksi et al. |
| 2011/0028950 | A1 | 2/2011 | Raksi et al. |
| 2011/0028951 | A1 | 2/2011 | Raksi et al. |
| 2011/0028952 | A1 | 2/2011 | Raksi et al. |
| 2011/0028953 | A1 | 2/2011 | Raksi et al. |
| 2011/0028954 | A1 | 2/2011 | Raksi et al. |
| 2011/0028955 | A1 | 2/2011 | Raksi |
| 2011/0028957 | A1 | 2/2011 | Raksi et al. |
| 2011/0028958 | A1 | 2/2011 | Raksi et al. |
| 2011/0172649 | A1* | 7/2011 | Schuele et al. ................... 606/4 |
| 2011/0251601 | A1* | 10/2011 | Bissmann et al. ............... 606/5 |
| 2012/0016349 | A1 | 1/2012 | Brownell |
| 2012/0182522 | A1* | 7/2012 | Frey ........................ A61B 3/14 351/206 |

FOREIGN PATENT DOCUMENTS

| | | |
|---|---|---|
| WO | 2007143111 A3 | 12/2008 |
| WO | 2009033111 A2 | 3/2009 |
| WO | 2009033111 A3 | 4/2009 |
| WO | WO 2011150431 A1 * | 12/2011 |

OTHER PUBLICATIONS

European Search Report for Application No. EP15193619, mailed on Feb. 29, 2016, 6 pages.

* cited by examiner

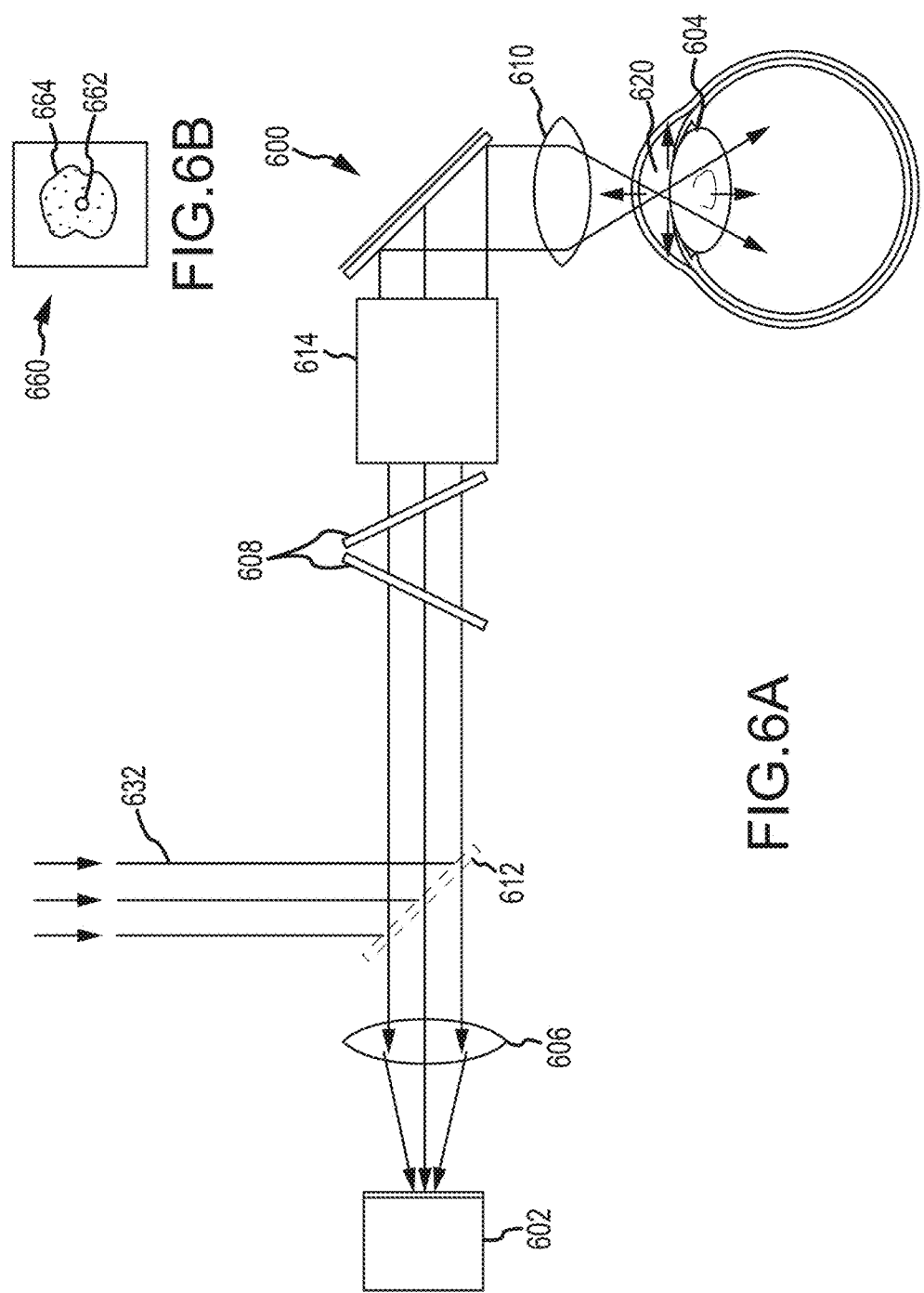

OPHTHALMIC RANGE FINDING

CROSS-REFERENCE TO RELATED APPLICATIONS

This application claims priority to Provisional U.S. Patent Application No. 61/637,644 filed Apr. 24, 2012, entitled "OPHTHALMIC RANGE FINDING" and Provisional U.S. Patent Application No. 61/500,596 filed Jun. 23, 2011, entitled "OPHTHALMIC RANGE FINDING." The entire disclosure of both aforementioned Provisional U.S. Patent Applications are hereby incorporated by reference, for all purposes, as if fully set forth herein.

BACKGROUND

Femtosecond lasers are commonly used to form incisions within corneal tissue to form a LASIK flap. Other ophthalmic treatments involve procedures performed on anatomical features within the eye, such as the capsular bag and lens. Such treatments may involve the removal of cataracts. To ascertain the location and orientation of the anatomical features within the eye (e.g., the capsular bag, lens, and the like), either prior to or during surgery, an optical coherence tomography (OCT) system may be used. Such systems, however, are generally expensive, limiting their potential acceptance.

BRIEF SUMMARY OF THE INVENTION

Embodiments of the present invention encompass methods and systems for analyzing the ophthalmic anatomy of a patient posterior to the cornea and/or for providing therapeutic treatment to the ophthalmic anatomy. According to one embodiment, a system for treating an eye of a patient is provided. The eye may include a fluid posterior to a cornea and the system may include a femtosecond laser, an optical system, a sensor, and a computing device. The femtosecond laser may be configured for directing femtosecond energy along a path and the optical system may be disposed along the path from the laser. The optical system may include a focusing lens and a scanner so as to scan a non-plasma-generating focus of the femtosecond energy along a path within the patient's eye. The path may extend posterior to the patient's cornea within the fluid so that the path includes a first location disposed within a tissue of the eye and a second location disposed within the cornea. The sensor may be oriented along the path so as to sense a first signal associated with a first focus location within the eye and a second signal associated with a second focus location within the eye. The computing device may be communicatively coupled with the sensor and may determine a location of an interface between the fluid and a tissue of the eye in response to the first signal and the second signal.

In some embodiments, the sensor may be configured for sensing the signals in response to the energy generating a plasma at the focus when the plasma is disposed in the fluid and when the focus is at the second location. The sensor may include an image acquisition device configured for acquiring tissue interface reflectance images and the computing device may be configured to determine the location of the fluid/tissue interface based on a comparison between the first reflectance image and the second reflectance image. In some embodiments, the sensor may be configured to sense a dimension of a spot size at the focus and the computing device may be configured to determine if the beam spot size is indicative of wrinkling associated with engagement between the cornea and a corneal-shaping patient interface of the system.

In one embodiment, the computing device is configured to receive OCT or other preoperative diagnostic data regarding the interface location. Alternatively or additionally, the computing device may be configured to determine and transmit pachymetry data for the eye. Alternatively or additionally, the computing device may be configured to determine a separation between a posterior capsule and a retina of the eye. Alternatively or additionally, the computing device may be configured to determine a curvature of a patient interface contact surface of the system. Alternatively or additionally, the computing device may be configured to detect bubbles at a meniscus between a patient interface contact surface of the system and the eye. Alternatively or additionally, the computing device may be configured to determine a location of an apex or vertex of a contact surface of a patient interface of the system. In one embodiment, the non-plasma-generating focus of the femtosecond energy may have an energy level less than a bubble formation threshold of the fluid or the tissue of the eye.

According to another embodiment, a machine-readable medium having machine-executable instructions configured to perform a method for analyzing the ophthalmic anatomy of a patient posterior to the cornea is provided. The method may include scanning a focus of a femtosecond laser beam along a path within the patient's eye. At least a portion of the path may be disposed posterior to the patient's cornea and the path may include a first location and a second location. The method may also include acquiring a first reflectance image associated with the focus disposed at the first location and acquiring a second reflectance image associated with the focus disposed at the second location. The method may further include determining the presence or absence of an ophthalmic anatomical feature of the eye based on a comparison between the first reflectance image and the second reflectance image.

In some embodiments, the first and/or second reflectance images may be acquired with a CCD camera. The anatomical feature may include a capsular bag, a lens, and/or other anatomical features. In some embodiments, a therapeutic energy may be maintained for the femtosecond laser beam during the scanning process to provide therapeutic treatment during the scanning process. The femtosecond laser beam (tissue identifying light) signals may be generated in response to differences in plasma formation when the focal point of the femtosecond laser is either scanned in the liquid vitreous between tissues of the eye and/or scanned within the tissues of the capsular bag, lens, or endothelial layers along the posterior of the cornea.

In some embodiments, the method may additionally include operating a laser to provide therapeutic treatment to one or more anatomical features. Providing a therapeutic treatment may include disrupting a capsular bag, a lens, or another anatomical feature. In one embodiment, the therapeutic treatment includes lens fragmentation, capsulorhexis, or capsulotomy. In one embodiment, the laser may be the femtosecond laser operated to scan the patient's eye, in which the femtosecond laser is operated at a higher energy level to provide the therapeutic treatment.

According to another embodiment, a system for analyzing the ophthalmic anatomy of an eye posterior to a cornea is provided. The system may include a femtosecond laser, an acquiring device, and a computing device. A plasma-generating focus of the femtosecond laser beam may be scanned along a path within the eye such that at least a portion of the path is disposed posterior to the cornea and the path includes a first location and a second location. The acquiring device may acquire a first reflectance image associated with the focus disposed at the first location and may acquire a second reflectance image associated with the focus disposed at the second location. The computing device may be communicatively coupled with the acquiring device so that the computing device may determine the presence or absence of an ophthalmic anatomical feature of the eye based on a comparison between the first reflectance image and the second reflectance image.

In some embodiment, the acquiring device may be configured for sensing the images in response to the plasma-generated at the focus when the focus is disposed in the first location and when the focus is at the second location.

BRIEF DESCRIPTION OF THE DRAWINGS

FIGS. 6A and B illustrate an optical system for performing diagnostic and/or therapeutic scans according to one embodiment of the present invention.

DETAILED DESCRIPTION OF THE INVENTION

Figure 1:
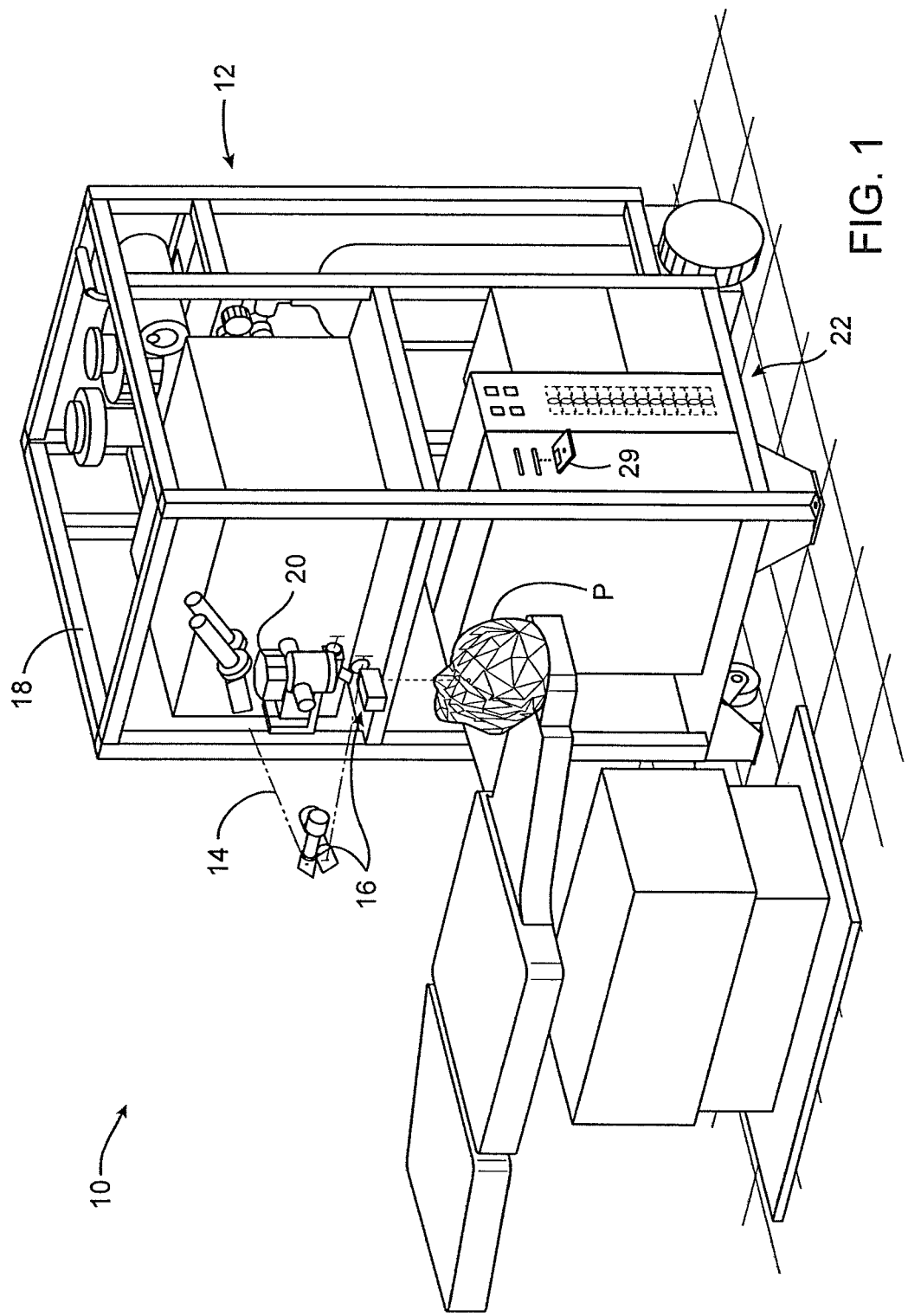
FIG. 1 illustrates a laser ablation system according to an embodiment of the present invention.

Embodiments of the present invention encompass methods and systems for analyzing the ophthalmic anatomy of a patient posterior to the cornea and/or for providing therapeutic treatment to the ophthalmic anatomy. The method may include scanning a focus of a femtosecond laser beam (or other laser beam) along a path within the patient's eye. A portion of the path may be disposed at the corneal endothelium or posterior to the patient's cornea and the path may include a first location and a second location. The method may also include acquiring a first reflectance image associated with the focus disposed at the first location and acquiring a second reflectance image associated with the focus disposed at the second location. The method may further include determining the presence or absence of an ophthalmic anatomical feature of the eye based on a comparison between the first reflectance image and the second reflectance image. The method may additionally include operating a laser beam to provide therapeutic treatment to one or more of the anatomical features. The laser beam used in therapeutic procedures may be the femtosecond laser used in the scanning process.

The first and second reflectance images may be acquired with a ccd camera or any other type of camera or image capture device. The anatomical feature may include a capsular bag and/or a lens within the capsular bag. The therapeutic treatment provided by the laser (e.g., the femtosecond laser) may include disrupting a capsule or lens. The femtosecond laser may be operated at a lower energy level during the scanning process and may be operated at a higher energy level to provide the therapeutic treatment.

In some embodiments, the therapeutic energy level of the femtosecond laser beam may be maintained or provided during the scanning process in order to provide the therapeutic treatment concurrent with or during the scanning process. In other words, the energy level of the femtosecond laser beam may be varied between a lower energy level and a higher energy level so that the therapeutic treatment and scan process may be performed nearly simultaneously. For example, a lower energy level may be used for the femtosecond laser beam to determine the location, orientation, and other properties of the capsular bag (or other anatomical feature) and subsequently, a higher energy level may be used to provide therapeutic treatment to the capsular bag (or other anatomical feature). In other embodiments, the therapeutic treatment may be provided while anatomical features are being scanned (i.e., during the scanning process).

The femtosecond laser beam signals/energy levels may be generated in response to differences in plasma formation when the focal point of the femtosecond laser is scanned in the liquid vitreous between tissues of the eye and/or scanned within the tissues of the capsular bag, lens, or endothelial layers along the posterior of the cornea. In other embodiments, therapeutic treatment may be provided subsequent to the scanning process.

The therapeutic treatments that may be performed with the femtosecond laser include lens fragmentation, capsulorhexis, capsulotomy, and the like. Capsulotomy procedures generally refer to procedures where the whole or a portion of the capsule is removed. Capsulorhexis procedures involve tearing or cutting away a portion of the capsule, and lens fragmentation procedures involve incising, disrupting, fragmenting, and/or breaking up the lens. Such treatments may be performed as part of an extracapsular cataract extraction procedure (ECCE), or commonly a cataract removal. The use of the femtosecond laser (or other laser) in the lens fragmentation process may reduce or eliminate corneal stress that may result from conventional phacoemulsification procedures involving ultrasound vibrations and probes. Further, use of the femtosecond laser in cataract removal procedures may provide the advantage of smaller capsular incisions while reducing the operator learning curve required for conventional phacoemulsification procedures using ultrasound vibrations and probes. This may reduce post-cataract removal complications.

Using the femtosecond laser and one or more therapeutic procedures described herein, the capsule may be incised for capsulotomy and/or the lens may be incised and broken into fragments prior to the capsulorhexis or laser capsulotomy, and vice versa, followed by insertion of a forcep or probe to withdraw the incised portion of the capsule and/or insertion of an aspiration probe to withdraw the severed portions of the lens. The femtosecond laser and system described herein may also be used for post cataract procedures, such as to cut or ablate clouded portions of the capsule subsequent to an ECCE procedure. The therapeutic treatment provided by the femtosecond laser may be extended to include the back surface of the lens making it possible to perform some pre-chop or cutting of the lens.

During the scanning process, the location, orientation (e.g., tilt), depth and the like of the capsule or lens within the eye may be determined. The focal point of the laser beam may be varied along orthogonal x, y, and z axes during such scanning procedures. Varying the laser beam's focal point in this manner and determining the location, orientation, and depth of anatomical features may be referred to as range finding. The laser beams used in such operations may be referred to as range finding lasers. The scanning process may also replace other preoperative procedures, such as keratometry testing to determine the strength of the intraocular lens (IOL) needed. Such testing may involve the femtosecond laser, which may be set at a low/scanning energy level.

The methods and systems described herein involve ocular diagnostic (i.e., range finding) and therapeutic treatment techniques. Such diagnostic or range finding techniques involve directing laser light from a femtosecond laser beam (or other laser source) to the eye in order to locate ophthalmic anatomy posterior to the cornea (e.g., capsular bag, lens, and the like). In therapeutic treatments, the light from the same femtosecond laser beam (or other laser) may be focused within the eye in order to disrupt tissue posterior to the cornea, and particularly tissue of the capsular bag or crystalline lens. The diagnostic applications of the femtosecond laser beam (i.e., range finding and/or therapeutic treatment) provided by the methods and systems described herein may be used in conjunction with conventional cataract removal systems and procedures, such as to range find various ophthalmic anatomy prior, during, or following such procedures.

In one embodiment, the laser light may be polarized. The polarized light may improve detection of the ophthalmic anatomy during diagnostic or range finding applications. In a specific embodiment, the light is circularly polarized rather than plane polarized. The circularly polarized light may be simpler to implement versus plane polarized and/or additionally improve detection of the ophthalmic anatomy during the diagnostic or range finding applications.

The crystalline lens or lens resides within the capsular bag, posterior to the cornea. It is often desirable to incise and selectively remove a portion of the capsular bag and/or lens within the capsular bag, such as for example during cataract surgery. According to embodiments of the invention, prior to such procedures (e.g., cataract surgery), the capsular bag and/or lens are located by scanning a femtosecond laser within the eye, and evaluating the resulting reflected light. The reflected light is generated by the interface between tissue layers of the eye. In some embodiments, the femtosecond laser light used for locating tissues (e.g., range finding) may be at a lower energy than that used for incising the capsular bag or lens.

In other embodiments, the scanning procedure and therapeutic procedure may occur in real time or roughly simultaneously. For example, a therapeutic energy level may be maintained when locating tissues, with the tissue identifying light signals being generated in response to differences in plasma formation when the focal point of the laser is scanned in the liquid vitreous between tissues of the eye, and/or scanned within tissues of the capsular bag, lens, or endothelial layers along the posterior of the cornea. In yet other embodiments, the energy level may be varied between a scanning energy level and a therapeutic energy level so that a therapeutic treatment (e.g., lens fragmentation, capsulorhexis, and the like) may be performed immediately after the ophthalmic anatomy (e.g., capsular bag, lens, and the like) is located.

Optionally, techniques may involve using a zoom beam expander (ZBX) to move the beam focal point throughout subcorneal depths, for example between 0 and 6 mm, along the optical axis, and detecting any changes in the index of refraction associated with corresponding reflected light. In some instances, results can be used to plan for capsulorhexis or capsule disrupting procedures.

Embodiments of the present invention can be readily adapted for use with existing laser systems and other optical treatment devices. Although system, software, and method embodiments of the present invention are described primarily in the context of a laser eye surgery system, it should be understood that embodiments of the present invention may be adapted for use in alternative eye treatment procedures, systems, or modalities, such as spectacle lenses, intraocular lenses, accommodating IOLs, contact lenses, corneal ring implants, collagenous corneal tissue thermal remodeling, corneal inlays, corneal onlays, other corneal implants or grafts, and the like. Relatedly, systems, software, and methods according to embodiments of the present invention are well suited for customizing any of these treatment modalities to a specific patient. Thus, for example, embodiments encompass custom intraocular lenses, custom contact lenses, custom corneal implants, and the like, which can be configured to treat or ameliorate any of a variety of vision conditions in a particular patient based on their unique ocular characteristics or anatomy.

Optical Systems

Turning now to the drawings, FIG. 1 illustrates a laser eye surgery system 10 of the present invention, including a laser 12 that produces a laser beam 14. Laser 12 is optically coupled to laser delivery optics 16, which directs laser beam 14 to an eye E of patient P. A delivery optics support structure (not shown here for clarity) extends from a frame 18 supporting laser 12. A microscope 20 is mounted on the delivery optics support structure, the microscope often being used to image a cornea of eye E.

Laser 12 may comprises a femtosecond laser capable of providing pulsed laser beams, which may be used in optical procedures, such as localized photodisruption (e.g., laser induced optical breakdown). Localized photodisruptions can be placed at or below the surface of the material to produce high-precision material processing. For example, a micro-optics scanning system may be used to scan the pulsed laser beam to produce an incision in the material, create a flap of material, create a pocket within the material, form removable structures of the material, and the like. The term "scan" or "scanning" refers to the movement of the focal point of the pulsed laser beam along a desired path or in a desired pattern.

To provide the pulsed laser beam, the laser 12 may utilize a chirped pulse laser amplification system, such as described in U.S. Pat. No. RE37,585, for photoalteration. U.S. Pat. Publication No. 2004/0243111 also describes other methods of photoalteration. Other devices or systems may be used to generate pulsed laser beams. For example, non-ultraviolet (UV), ultrashort pulsed laser technology can produce pulsed laser beams having pulse durations measured in femtoseconds. Some of the non-UV, ultrashort pulsed laser technology may be used in ophthalmic applications. For example, U.S. Pat. No. 5,993,438 discloses a device for performing ophthalmic surgical procedures to effect high-accuracy corrections of optical aberrations. U.S. Pat. No. 5,993,438 discloses an intrastromal photodisruption technique for reshaping the cornea using a non-UV, ultrashort (e.g., femtosecond pulse duration), pulsed laser beam that propagates through corneal tissue and is focused at a point below the surface of the cornea to photodisrupt stromal tissue at the focal point.

The system 10 is capable of generating the pulsed laser beam 14 with physical characteristics similar to those of the laser beams generated by a laser system disclosed in U.S. Pat. No. 4,764,930, U.S. Pat. No. 5,993,438, or the like. For example, the system 10 can produce a non-UV, ultrashort pulsed laser beam for use as an incising laser beam. This pulsed laser beam preferably has laser pulses with durations as long as a few nanoseconds or as short as a few femtoseconds. For intrastromal photodisruption of the tissue, the pulsed laser beam 14 has a wavelength that permits the pulsed laser beam 14 to pass through the cornea without absorption by the corneal tissue. The wavelength of the pulsed laser beam 14 is generally in the range of about 3 microns to about 1.9 nm, preferably between about 400 nm to about 3000 nm, and the irradiance of the pulsed laser beam 14 for accomplishing photodisruption of stromal tissues at the focal point is greater than the threshold for optical breakdown of the tissue. Although a non-UV, ultrashort pulsed laser beam is described in this embodiment, the laser 12 produces a laser beam with other pulse durations and different wavelengths in other embodiments.

In this embodiment, the delivery optics 16 direct the pulsed laser beam 14 toward the eye (e.g., onto the cornea) for plasma mediated (e.g., non-UV) photoablation of superficial tissue, or into the stroma for intrastromal photodisruption of tissue. The system 10 may also include an applanation lens (not shown) to flatten the cornea prior to scanning the pulsed laser beam 14 toward the eye. A curved, or non-planar, lens may substitute this applanation lens to contact the cornea in other embodiments.

Laser system 10 will generally include a computer or programmable processor 22. Processor 22 may comprise (or interface with) a conventional PC system including the standard user interface devices such as a keyboard, a display monitor, and the like. Processor 22 will typically include an input device such as a magnetic or optical disk drive, an Internet connection, or the like. Such input devices will often be used to download a computer executable code from a tangible storage media 29 embodying any of the methods of the present invention. Tangible storage media 29 may take the form of a floppy disk, an optical disk, a data tape, a volatile or non-volatile memory, RAM, or the like, and the processor 22 will include the memory boards and other standard components of modern computer systems for storing and executing this code. Tangible storage media 29 may optionally embody wavefront sensor data, wavefront gradients, a wavefront elevation map, a treatment map, a corneal elevation map, and/or an ablation table. While tangible storage media 29 will often be used directly in cooperation with an input device of processor 22, the storage media may also be remotely operatively coupled with processor by means of network connections such as the Internet, and by wireless methods such as infrared, Bluetooth, or the like.

Laser 12 and delivery optics 16 will generally direct laser beam 14 to the eye of patient P under the direction of a computer 22. Computer 22 will often selectively adjust laser beam 14 to expose portions of the cornea to the pulses of laser energy so as to effect a predetermined sculpting of the cornea and alter the refractive characteristics of the eye. In many embodiments, both laser beam 14 and the laser delivery optical system 16 will be under computer control of processor 22 to effect the desired laser incising or sculpting process, with the processor effecting (and optionally modifying) the pattern of laser pulses. The pattern of pulses may by summarized in machine readable data of tangible storage media 29 in the form of a treatment table, and the treatment table may be adjusted according to feedback input into processor 22 from an automated image analysis system in response to feedback data provided from an ablation monitoring system feedback system. Optionally, the feedback may be manually entered into the processor by a system operator. Such feedback might be provided by integrating the wavefront measurement system described below with the laser treatment system 10, and processor 22 may continue and/or terminate a sculpting treatment in response to the feedback, and may optionally also modify the planned sculpting based at least in part on the feedback. Measurement systems are further described in U.S. Pat. No. 6,315,413, the full disclosure of which is incorporated herein by reference.

Laser beam 14 may be adjusted to produce the desired incisions or sculpting using a variety of alternative mechanisms. The laser beam may also be tailored by varying the size and offset of the laser spot from an axis of the eye, as described in U.S. Pat. Nos. 5,683,379, 6,203,539, and 6,331,177, the full disclosures of which are incorporated herein by reference.

Still further alternatives are possible, including scanning of the laser beam over the surface of the eye and controlling the number of pulses and/or dwell time at each location, as described, for example, by U.S. Pat. No. 4,665,913, the full disclosure of which is incorporated herein by reference;

using masks in the optical path of laser beam 14 which ablate to vary the profile of the beam incident on the cornea, as described in U.S. Pat. No. 5,807,379, the full disclosure of which is incorporated herein by reference; hybrid profile-scanning systems in which a variable size beam (typically controlled by a variable width slit and/or variable diameter iris diaphragm) is scanned across the cornea; or the like. The computer programs and control methodology for these laser pattern tailoring techniques are well described in the patent literature.

Additional components and subsystems may be included with laser system 10, as should be understood by those of skill in the art. Further details of suitable systems can be found in commonly assigned U.S. Publication Nos. 20090247997 and 20090247998, the complete disclosures of which are incorporated herein by reference. Suitable systems also include commercially available femtosecond laser systems such as those manufactured and/or sold by Alcon, Technolas, Nidek, WaveLight, Schwind, Zeiss-Meditec, Ziemer, and the like.

The delivery optics 16 may include a scanner that operates at pulse repetition rates between about 10 kHz and about 400 kHz, or at any other desired rate. In one embodiment, the scanner generally moves the focal point of the pulsed laser beam 14 through the desired scan pattern at a substantially constant scan rate while maintaining a substantially constant separation between adjacent focal points of the pulsed laser beam 14. The step rate at which the focal point of the laser beam 14 is moved is referred to herein as the scan rate. The scan rates may be selected from a range between about 30 MHz and about 1 GHz with a pulse width in a range between about 300 picoseconds and about 10 femtoseconds, although other scan rates and pulse widths may be used. Further details of laser scanners are known in the art, such as described, for example, in U.S. Pat. No. 5,549,632, the entire disclosure of which is incorporated herein by reference.

In one embodiment, the scanner utilizes a pair of scanning mirrors or other optics (not shown) to angularly deflect and scan the pulsed laser beam 14. For example, scanning mirrors driven by galvanometers may be employed where each of the mirrors scans the pulsed laser beam 14 along one of two orthogonal axes. A focusing objective (not shown), whether one lens or several lenses, images the pulsed laser beam 14 onto a focal plane of the system 10. The focal point of the pulsed laser beam 14 may thus be scanned in two dimensions (e.g., the x-axis and the y-axis) within the focal plane of the system 10. Scanning along the third dimension, i.e., moving the focal plane along an optical axis (e.g., the z-axis), may be achieved by moving the focusing objective, or one or more lenses within the focusing objective, along the optical axis.

Figure 2:
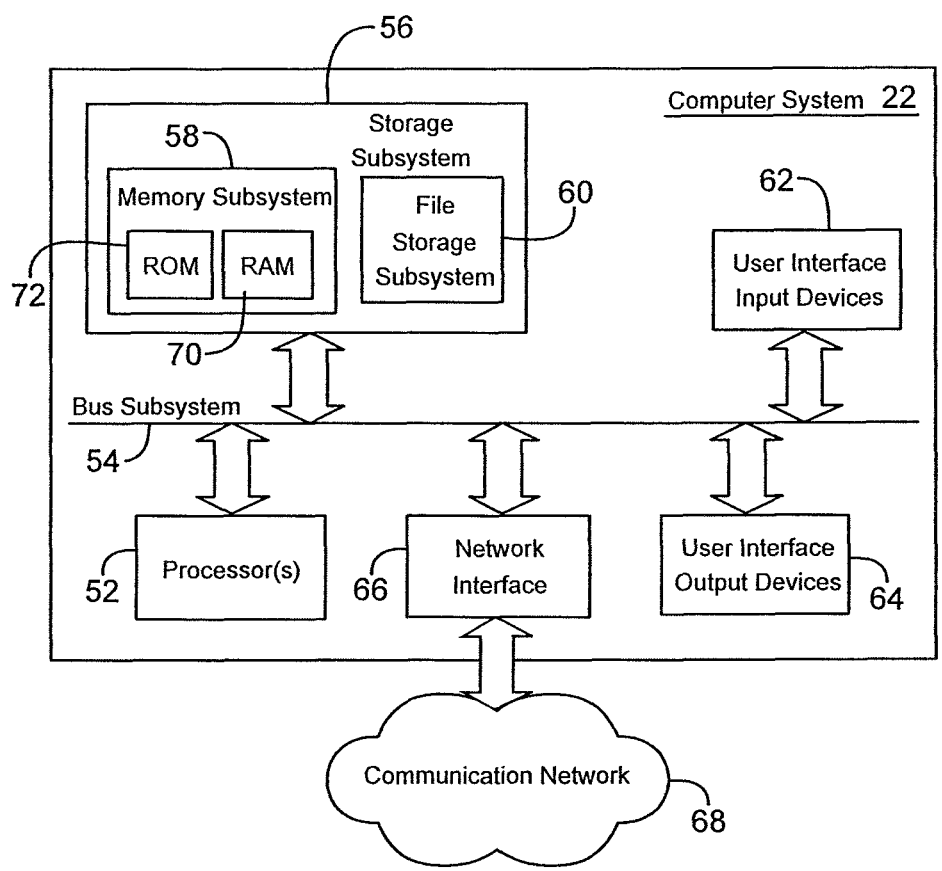
FIG. 2 illustrates a simplified computer system according to an embodiment of the present invention.

FIG. 2 is a simplified block diagram of an exemplary computer system 22 that may be used by the laser surgical system 10 of the present invention. Computer system 22 typically includes at least one processor 52 which may communicate with a number of peripheral devices via a bus subsystem 54. These peripheral devices may include a storage subsystem 56, comprising a memory subsystem 58 and a file storage subsystem 60, user interface input devices 62, user interface output devices 64, and a network interface subsystem 66. Network interface subsystem 66 provides an interface to outside networks 68 and/or other devices, such as the wavefront measurement system 30.

User interface input devices 62 may include a keyboard, pointing devices such as a mouse, trackball, touch pad, or graphics tablet, a scanner, foot pedals, a joystick, a touch-screen incorporated into the display, audio input devices such as voice recognition systems, microphones, and other types of input devices. User input devices 62 will often be used to download a computer executable code from a tangible storage media 29 embodying any of the methods of the present invention. In general, use of the term "input device" is intended to include a variety of conventional and proprietary devices and ways to input information into computer system 22.

User interface output devices 64 may include a display subsystem, a printer, a fax machine, or non-visual displays such as audio output devices. The display subsystem may be a cathode ray tube (CRT), a flat-panel device such as a liquid crystal display (LCD), a projection device, or the like. The display subsystem may also provide a non-visual display such as via audio output devices. In general, use of the term "output device" is intended to include a variety of conventional and proprietary devices and ways to output information from computer system 22 to a user.

Storage subsystem 56 can store the basic programming and data constructs that provide the functionality of the various embodiments of the present invention. For example, a database and modules implementing the functionality of the methods of the present invention, as described herein, may be stored in storage subsystem 56. These software modules are generally executed by processor 52. In a distributed environment, the software modules may be stored on a plurality of computer systems and executed by processors of the plurality of computer systems. Storage subsystem 56 typically comprises memory subsystem 58 and file storage subsystem 60.

Memory subsystem 58 typically includes a number of memories including a main random access memory (RAM) 70 for storage of instructions and data during program execution and a read only memory (ROM) 72 in which fixed instructions are stored. File storage subsystem 60 provides persistent (non-volatile) storage for program and data files, and may include tangible storage media 29 (FIG. 1) which may optionally embody wavefront sensor data, wavefront gradients, a wavefront elevation map, a treatment map, and/or an ablation table. File storage subsystem 60 may include a hard disk drive, a floppy disk drive along with associated removable media, a Compact Digital Read Only Memory (CD-ROM) drive, an optical drive, DVD, CD-R, CD-RW, solid-state removable memory, and/or other removable media cartridges or disks. One or more of the drives may be located at remote locations on other connected computers at other sites coupled to computer system 22. The modules implementing the functionality of the present invention may be stored by file storage subsystem 60.

Bus subsystem 54 provides a mechanism for letting the various components and subsystems of computer system 22 communicate with each other as intended. The various subsystems and components of computer system 22 need not be at the same physical location but may be distributed at various locations within a distributed network. Although bus subsystem 54 is shown schematically as a single bus, alternate embodiments of the bus subsystem may utilize multiple busses.

Computer system 22 itself can be of varying types including a personal computer, a portable computer, a workstation, a computer terminal, a network computer, a control system in a wavefront measurement system or laser surgical system, a mainframe, or any other data processing system. Due to the ever-changing nature of computers and networks, the description of computer system 22 depicted in FIG. 2 is intended only as a specific example for purposes of illustrating one embodiment of the present invention. Many other configurations of computer system 22 are possible having more or less components than the computer system depicted in FIG. 2.

Figure 3:
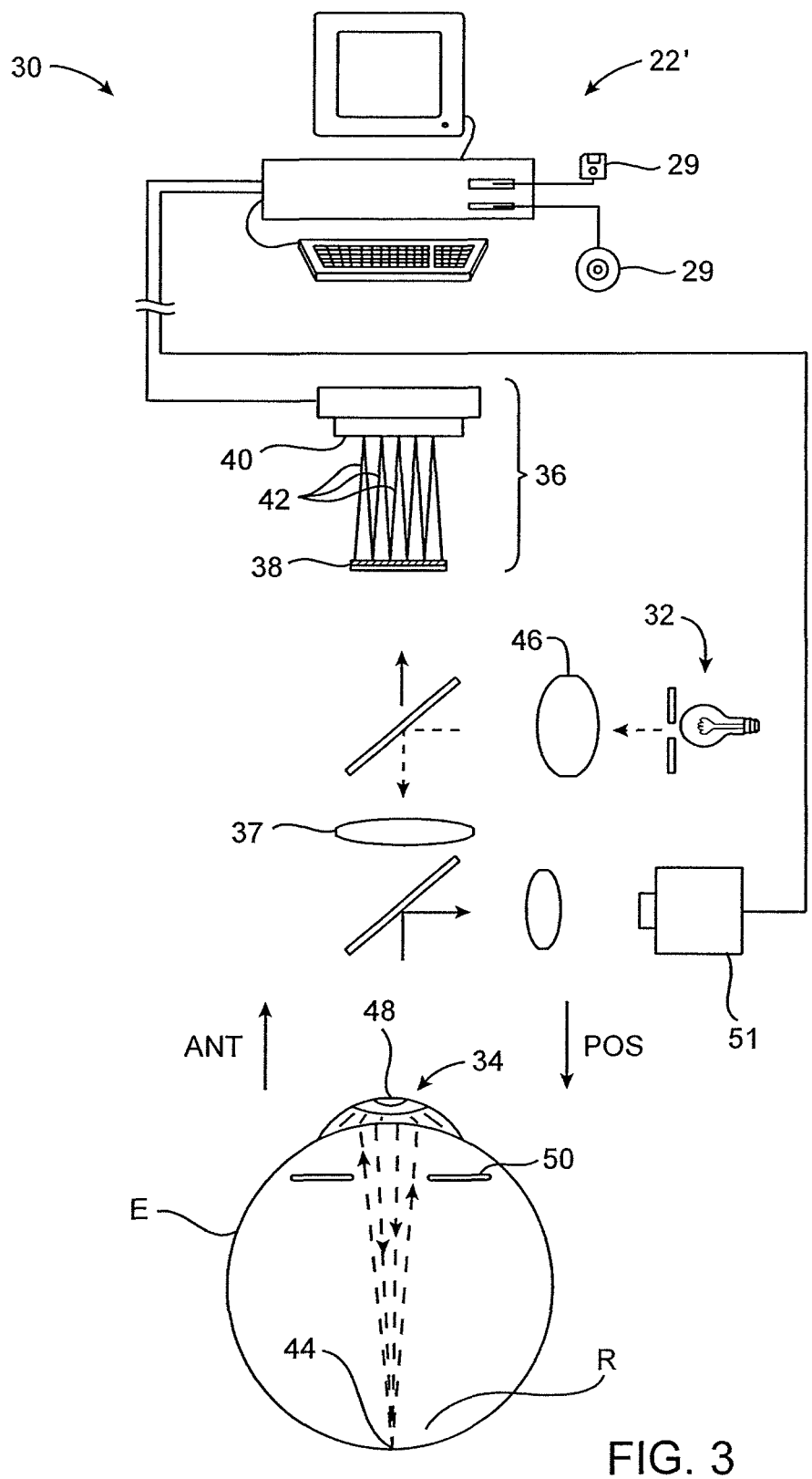
FIG. 3 illustrates a wavefront measurement system according to an embodiment of the present invention.

Referring now to FIG. 3, one embodiment of a wavefront measurement system 30 is schematically illustrated in simplified form. In very general terms, wavefront measurement system 30 is configured to sense local slopes of a gradient map exiting the patient's eye. Devices based on the Hartmann-Shack principle generally include a lenslet array to sample the gradient map uniformly over an aperture, which is typically the exit pupil of the eye. Thereafter, the local slopes of the gradient map are analyzed so as to reconstruct the wavefront surface or map.

More specifically, one wavefront measurement system 30 includes an image source 32, such as a laser, which projects a source image through optical tissues 34 of eye E so as to form an image 44 upon a surface of retina R. The image from retina R is transmitted by the optical system of the eye (e.g., optical tissues 34) and imaged onto a wavefront sensor 36 by system optics 37. The wavefront sensor 36 communicates signals to a computer system 22' for measurement of the optical errors in the optical tissues 34 and/or determination of an optical tissue ablation treatment program. Computer 22' may include the same or similar hardware as the computer system 22 illustrated in FIGS. 1 and 2. Computer system 22' may be in communication with computer system 22 that directs the laser surgery system 10, or some or all of the components of computer system 22, 22' of the wavefront measurement system 30 and laser surgery system 10 may be combined or separate. If desired, data from wavefront sensor 36 may be transmitted to a laser computer system 22 via tangible media 29, via an I/O port, via a networking connection 66 such as an intranet or the Internet, or the like.

Wavefront sensor 36 generally comprises a lenslet array 38 and an image sensor 40. As the image from retina R is transmitted through optical tissues 34 and imaged onto a surface of image sensor 40 and an image of the eye pupil P is similarly imaged onto a surface of lenslet array 38, the lenslet array separates the transmitted image into an array of beamlets 42, and (in combination with other optical components of the system) images the separated beamlets on the surface of sensor 40. Sensor 40 typically comprises a charged couple device or "CCD," and senses the characteristics of these individual beamlets, which can be used to determine the characteristics of an associated region of optical tissues 34. In particular, where image 44 comprises a point or small spot of light, a location of the transmitted spot as imaged by a beamlet can directly indicate a local gradient of the associated region of optical tissue.

Eye E generally defines an anterior orientation ANT and a posterior orientation POS. Image source 32 generally projects an image in a posterior orientation through optical tissues 34 onto retina R as indicated in FIG. 3. Optical tissues 34 again transmit image 44 from the retina anteriorly toward wavefront sensor 36. Image 44 actually formed on retina R may be distorted by any imperfections in the eye's optical system when the image source is originally transmitted by optical tissues 34. Optionally, image source projection optics 46 may be configured or adapted to decrease any distortion of image 44.

In some embodiments, image source optics 46 may decrease lower order optical errors by compensating for spherical and/or cylindrical errors of optical tissues 34. Higher order optical errors of the optical tissues may also be compensated through the use of an adaptive optic element, such as a deformable mirror (described below). Use of an image source 32 selected to define a point or small spot at image 44 upon retina R may facilitate the analysis of the data provided by wavefront sensor 36. Distortion of image 44 may be limited by transmitting a source image through a central region 48 of optical tissues 34 which is smaller than a pupil 50, as the central portion of the pupil may be less prone to optical errors than the peripheral portion. Regardless of the particular image source structure, it will be generally be beneficial to have a well-defined and accurately formed image 44 on retina R.

In one embodiment, the wavefront data may be stored in a computer readable medium 29 or a memory of the wavefront sensor system 30 in two separate arrays containing the x and y wavefront gradient values obtained from image spot analysis of the Hartmann-Shack sensor images, plus the x and y pupil center offsets from the nominal center of the Hartmann-Shack lenslet array, as measured by the pupil camera 51 (FIG. 3) image. Such information contains all the available information on the wavefront error of the eye and is sufficient to reconstruct the wavefront or any portion of it. In such embodiments, there is no need to reprocess the Hartmann-Shack image more than once, and the data space required to store the gradient array is not large. For example, to accommodate an image of a pupil with an 8 mm diameter, an array of a 20×20 size (i.e., 400 elements) is often sufficient. As can be appreciated, in other embodiments, the wavefront data may be stored in a memory of the wavefront sensor system in a single array or multiple arrays.

While the methods of the present invention will generally be described with reference to sensing of an image 44, a series of wavefront sensor data readings may be taken. For example, a time series of wavefront data readings may help to provide a more accurate overall determination of the ocular tissue aberrations. As the ocular tissues can vary in shape over a brief period of time, a plurality of temporally separated wavefront sensor measurements can avoid relying on a single snapshot of the optical characteristics as the basis for a refractive correcting procedure. Still further alternatives are also available, including taking wavefront sensor data of the eye with the eye in differing configurations, positions, and/or orientations. For example, a patient will often help maintain alignment of the eye with wavefront measurement system 30 by focusing on a fixation target, as described in U.S. Pat. No. 6,004,313, the full disclosure of which is incorporated herein by reference. By varying a position of the fixation target as described in that reference, optical characteristics of the eye may be determined while the eye accommodates or adapts to image a field of view at a varying distance and/or angles.

The location of the optical axis of the eye may be verified by reference to the data provided from a pupil camera 52. In the exemplary embodiment, a pupil camera 52 images pupil 50 so as to determine a position of the pupil for registration of the wavefront sensor data relative to the optical tissues.

Figure 3A:
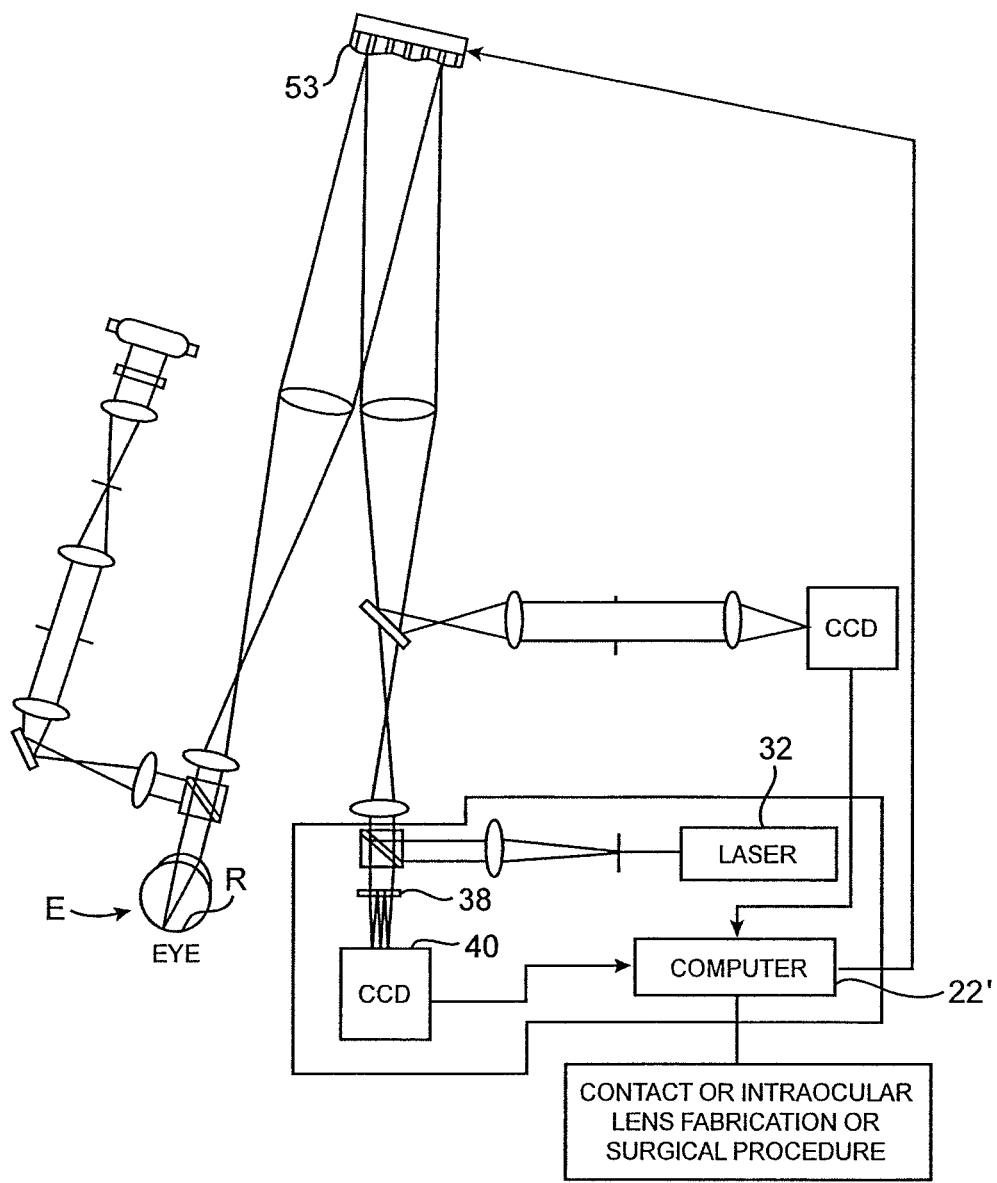
FIG. 3A illustrates another wavefront measurement system according to an embodiment of the present invention.

An alternative embodiment of a wavefront measurement system is illustrated in FIG. 3A. The major components of the system of FIG. 3A are similar to those of FIG. 3. Additionally, FIG. 3A includes an adaptive optical element 53 in the form of a deformable mirror. The source image is reflected from deformable mirror 98 during transmission to retina R, and the deformable mirror is also along the optical path used to form the transmitted image between retina R and imaging sensor 40. Deformable mirror 98 can be controllably deformed by computer system 22 to limit distortion of the image formed on the retina or of subsequent images formed of the images formed on the retina, and may enhance the accuracy of the resultant wavefront data. The structure and use of the system of FIG. 3A are more fully described in U.S. Pat. No. 6,095,651, the full disclosure of which is incorporated herein by reference.

The components of an embodiment of a wavefront measurement system for measuring the eye and ablations may comprise elements of a WaveScan® system, available from AMO Manufacturing USA, LLC, Milpitas, Calif. One embodiment includes a WaveScan system with a deformable mirror as described above. An alternate embodiment of a wavefront measuring system is described in U.S. Pat. No. 6,271,915, the full disclosure of which is incorporated herein by reference. It is appreciated that any wavefront aberrometer could be employed for use with the present invention. Relatedly, embodiments of the present invention encompass the implementation of any of a variety of optical instruments provided by WaveFront Sciences, Inc., including the COAS wavefront aberrometer, the ClearWave contact lens aberrometer, the CrystalWave IOL aberrometer, and the like.

Optical Systems for Therapeutic and/or Diagnostic Scanning

Figure 4:
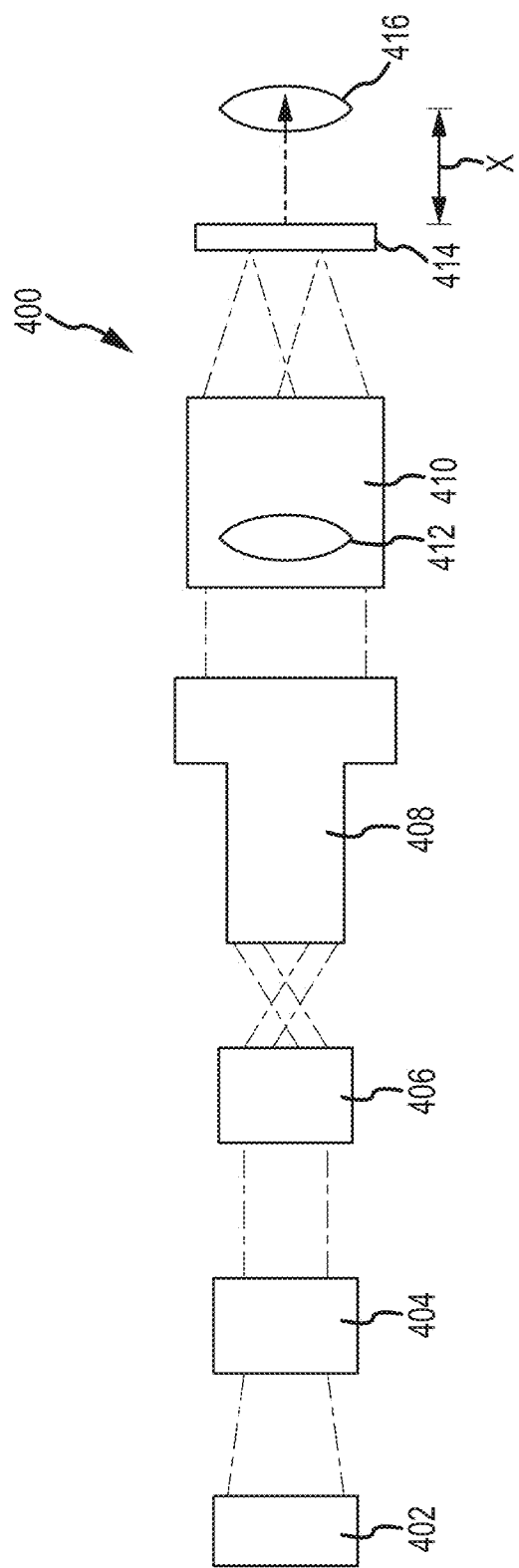
FIG. 4 illustrates an optical system for performing diagnostic and/or therapeutic scans according to one embodiment of the present invention.

Referring now to FIG. 4, illustrated is an optical system 400 according to one embodiment of the present invention. In some embodiments the optical system corresponds to an Intralase laser system or other laser system. Optical system 400 includes a laser source 402 that emits a laser beam. Laser light exiting laser source 402 may pass through a mirror path (not shown). The laser light may then be passed to a beam expander module 404. Beam expander module 404 may have a variable power that may range from about 2× to about 5× so that the system can be tuned to the laser parameters of the particular laser source 402. In one embodiment, beam expander module 404 is variable between about 2.8× and about 4×. In another embodiment, beam expander module 404 comprises a power of about 2×.

Optical system 400 may also include galvo block module 406. In one embodiment, galvo bock module 406 includes 2 mirrors that provide two dimensional scanning of the laser beam: one for x axis motion of the laser beam and one for y axis motion of the laser beam. In another embodiment, galvo block module 406 includes 3 mirrors, which operate to keep the laser beam centered as the laser beam exits galvo block module 406 and/or enters the next assembly. Optical system 400 may further include zoom beam expander 408. In some embodiments zoom beam expander 408 has a 6× power, which expands the laser beam by a factor of 6. In addition, zoom beam expander 408 may have a large field of view on the input side. Beam expander module 408 may function similar to an afocal telescope. Elements within zoom beam expander 408 may be adjustable to allow the depth of a laser beam's focal point to be adjusted a distance X along the optical axis (i.e., allow z axis scanning). The adjustable elements may include a doublet lens that provides a 150 mm focal length. The laser beams' focal point may be adjusted or varied a distance X along the optical axis between a first anatomical feature 414 (e.g., capsule, cornea, and the like) and a second anatomical feature 416 (e.g., lens). In some embodiments, the variable distance X ranges between 0 and 6 mm, although others depths are possible. Such variance may allow the focal point of the laser beam to be adjusted from above the top of the cornea to a position below the lens. In other embodiments, the focal point depth may be adjusted to deeper depths, such as posterior to the capsule and/or retina.

In addition to varying the depth of the focal point, zoom beam expander 408 may also correct or compensate for aberrations to maintain the laser beam focal spot quality. Correcting or compensating for aberrations may involve the application of an applanation lens as described herein or application or different optics configurations. Further details of suitable systems or optical configurations can be found in U.S. Publication Nos. 20110028948, 20110028949, 20110028950, 20110028951, 20110028952, 20110028953, 20110028954, 20110028955, 20110028957, and 20110028958, the complete disclosures of which are incorporated herein by reference.

In another embodiment, zoom beam expander 408 may not vary the depth of the focal point. Rather, additional optics (not shown) may be removably coupled with optical system 400 to vary the depth of the laser beam's focal point and/or provide lens fragmentation, capsulorhexis, capsulotomy, and/or other therapeutic treatments. The additional optics may have a lower depth variance range, such as 2-4 mm, although a full depth range of motion may be provided in some embodiments. The additional optics may be removed when the diagnostic scan and/or therapeutic treatment is complete so that other procedures may be performed, such as corneal flap cutting.

Optical system 400 may additionally include a focusing objective 410, which receives collimated light from zoom beam expander 408. Focusing objective 410 focuses the laser beam to a focal point via lens 412. The spot size of the focused laser beam may be variable. In some embodiments, the spot size may vary between 1 and 5 microns. In other embodiments, the spot size may be about 1.2 microns.

Some embodiments may involve performing a surgical or therapeutic procedure on anatomical features of the eye, such as the lens, capsule, and the like. Surgical or therapeutic procedures may involve capsulotomy, capsulorhexis, lens fragmentation, or other procedures. Capsulorhexis may involve incising a portion of the capsule to remove the lens and/or incising a portion of the capsule for removal. Lens fragmentation may include incising, breaking up, or disrupting a portion of the lens or the entire lens. The incision may be performed with a femtosecond laser, eliminating the need for a surgeon to manually cut away portions of the capsule or use ultrasound probes to break up the lens. The femtosecond laser beam may be operated at high energy levels during such therapeutic procedures. For example, depending on the pulse width, the pulse energy can be between about 0.01 microJoules to about 50 microJoules.

The femtosecond laser may also be operated in range finding procedures to scan the interior of a patient's eye to determine a location, depth, and/or orientation of the lens, capsule, and/or other anatomical feature. The femtosecond laser beam is typically operated at low energy levels during range finding/diagnostic scanning procedures such that the femtosecond energy imparted to the specific ocular tissue or fluid at the focus of the beam is less than the plasma generation threshold or photodisruption threshold for the specific ocular tissue or fluid (e.g., capsular bag, lens, aqueous humor, cornea, and the like), more preferably less than the energy threshold for bubble formation in the specific ocular tissue or fluid, and even more preferably at a fraction of the energy threshold for bubble formation in the specific ocular tissue or fluid (e.g., about ten percent (10%) of the energy threshold for bubble formation in the specific ocular tissue or fluid). In other embodiments, range finding/diagnostic scanning can be performed while the femtosecond laser beam is operated at energy levels for performing surgical or therapeutic procedures (e.g., greater than the photodisruption threshold). Range finding or scanning the eye's interior may involve moving a focus of the femtosecond laser beam (or other laser beam) along a path within the patient's eye. A portion of the path or the entire path may be disposed posterior to the patient's cornea and the path may include a plurality of locations along the path that are scanned. Scanning the interior of the eye (i.e., range finding) may provide a 2D or 3D image of anatomical features within the eye. Images of the eye may be captured by a camera, such as the ccd camera described herein. Range finding or diagnostic scanning may be performed prior to or concurrent with surgical or therapeutic procedures, such as capsulorhexis, lens fragmentation, capsulotomy, and the like. Range finding, and specifically the variable depth of the laser beam's focal point, may allow both the back and front surface of the lens, capsule, and/or other anatomical feature to be mapped.

The therapeutic and/or diagnostic scanning procedures described herein may be provided in a field upgrade unit that may be removably coupled with pre-existing laser optical systems. The field upgrade unit may allow both diagnostic scanning and therapeutic procedures to be performed on a pre-existing laser optical machine. The field upgrade unit may include a lens, camera, and semi-transparent mirror, such as mirror 612, lens 606, and camera 602 of FIG. 6A. The field upgrade unit may be retrofitted to pre-existing laser optical systems. Field retrofitting may involve a turret between components of the optical system or may be seamlessly fit in-line with other components of the optical system.

Figure 5A:
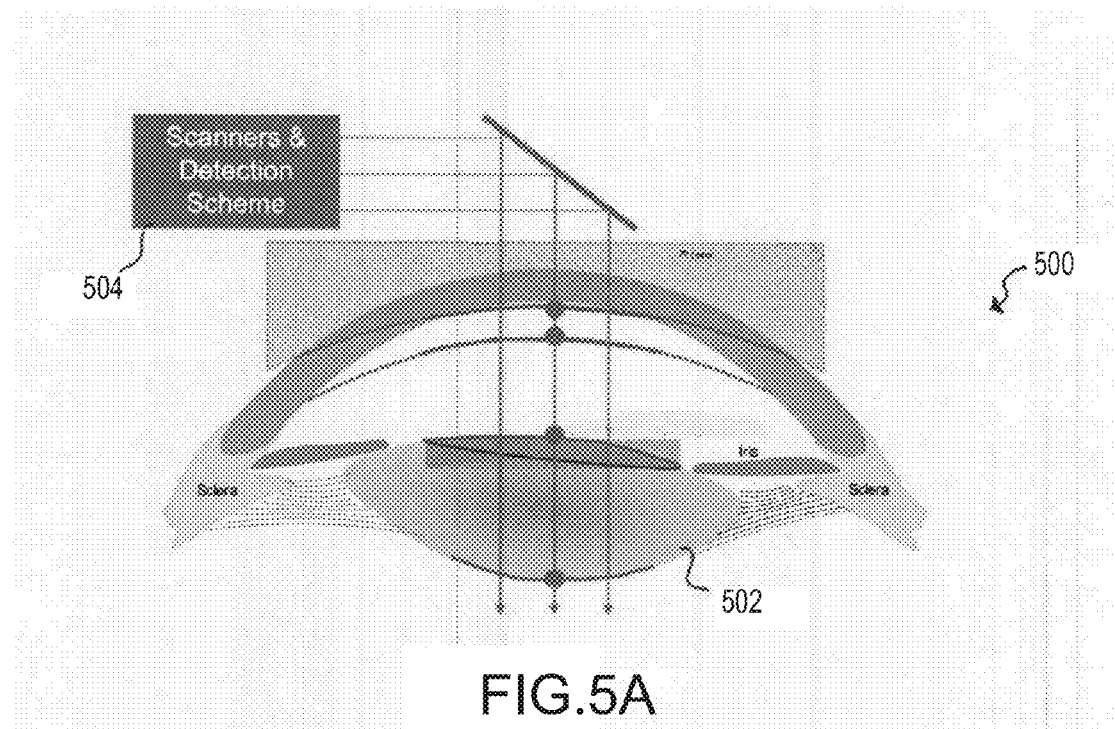
FIGS. 5A and B illustrate a diagnostic scan that may be performed to determine the location, depth, and orientation of an anatomical feature of the eye according to one embodiment of the present invention.

FIGS. 5A and B illustrate an example of a range finding or diagnostic scanning procedure performed to identify anatomical features of the eye. FIG. 5A illustrates that the optical system may be used to determine a location and/or orientation of a capsular bag 502 within eye 500. Specifically, an ophthalmic measurement device 504 (e.g., scanner and/or detection device) may receive laser light reflected from capsular bag 502 to determine conditions associated with the capsular bag 502. For example, ophthalmic measurement device 504 may determine that capsular bag 502 and/or a lens (not shown) comprise a tilted orientation. Similarly, ophthalmic measurement device 504 may determine a depth of capsular bag 502 and/or lens within the eye. Based on these detected conditions, one or more therapeutic treatments (e.g., capsulorhexis, lens fragmentation, capsulotomy, and the like) may be calculated and/or adjusted to account for the location, tilt, and/or depth of capsular bag 502 and/or the lens. The optical system may then be used to provide such treatments.

In one embodiment, the laser light may be polarized. The polarized light may be used during the range finding or diagnostic scanning procedure, although in some embodiments, the polarized light is additionally or alternatively used during therapeutic procedures. The polarized light may improve identification of anatomical features of the eye during the range finding or diagnostic scanning procedure. In a specific embodiment, the light is circularly polarized rather than plane polarized, which may improve implementation of the polarized light and/or identification of the anatomical features of the eye.

Figure 5B:
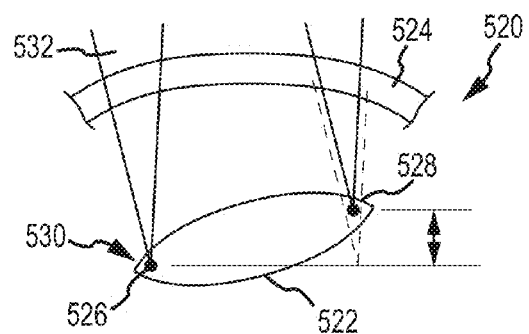

FIG. 5B illustrates an embodiment of measuring the orientation, location, depth, and/or other conditions of an anatomical feature of the eye 520. The eye 520 may have a substantially flattened cornea 524 with a lens 522 positioned posterior to cornea 524. Cornea 524 may be flattened due to the application of an applanation lens (not shown) to the cornea. Although cornea 524 is shown having a flattened configuration, it should be realized that cornea 524 may comprise various other configurations (e.g., round and the like). Lens 522 may be tilted with respect to cornea 524. Lens 522 may be scanned with the optical system to determine the amount of tilt, position, and/or depth of lens 522. The tilted orientation of lens 522 may be determined by varying the depth of the focal point 530 of laser beam 532 along the optical axis and scanning laser beam 532 across lens 522. For example, the depth and location of a first position 526 toward an exterior edge of lens 522 may be measured by scanning the focal point 530 of laser beam 532 to the first position 526. Laser light may be reflected at the first position 526 and detected by an ophthalmic measurement device 504 to determine that the focal point 530 of laser beam 532 is at or near an exterior edge of lens 522.

Similarly, the focal point 530 of laser beam 532 may be scanned to a second position 528 toward an opposite exterior edge of lens 522. Since the focal plane of laser beam 532 is planar, the focal point position is scanned from the focal plane associated with the first point 526 to the focal plane associated with point 528 (shown by the arrow) via a focusing objective or other device. The depth and location of the second position 528 may be measured by laser light reflected to the scanner or detection system 504 from second position 528. Other positions of lens 522 may similarly be measured. The tilt, depth, position, and other properties of lens 522 may be determined based on the measured first and second positions, 526 and 528, and/or other positions of lens 522.

In one embodiment, varying the depth and position of the focal point 530 of laser beam 532 may include scanning a ring field. The focal point 530 of laser beam 532 may be scanned in a corkscrew pattern where laser beam 532 is scanned in a circular pattern and the depth is reduced (or increased) incrementally for subsequent circles. At some point the focal point 530 will intersect first position 526 and second position 528 and other positions on the surface of lens 522. The positions may each be measured and recorded.

In some embodiments, therapeutic procedures may be provided as laser beam 532 is moved in the corkscrew pattern or other pattern. For example, laser beam 532 may be at a sufficiently high irradiance at focal point 530 to cause material breakdown. As the focal point 530 intersects with the capsule and the capsule is scanned, capsulorhexis may occur. Lens fragmentation, capsulotomy, and/or other therapeutic treatments may likewise be performed.

Referring now to FIG. 6A, illustrated is an embodiment of an optical system 600 capable of scanning/mapping anatomical features of an eye and/or providing therapeutic treatment thereto. Optical system 600 includes a camera 602, such as a ccd camera, that captures images (660 of FIG. 6B) of anatomical features 604 of the eye. Camera 602 may also represent a sensitive photodiode or quadrant detector, which may provide faster, more sensitive, and less expensive image capture than a ccd camera. A beam splitter can be used to couple out light for camera 602. The arrows on laser beam 632 indicate that laser beam 632 is focused on an anatomical feature 604 of the eye and that some laser light is reflected back to camera 602 through lens 606. Mirrors 608 represent two axis tilting galvo mirrors, although other galvo mirror configurations are possible (e.g., 3 galvo mirror configuration). Optical system 600 may include additional mirrors as well.

Light emitted by the femtosecond laser (or other laser) is collected and collimated by the objective 610 and/or zoom beam expander 614. The laser beam is focused at focal point 620 within or on a surface of the eye. A portion of the light that is reflected back is transmitted through mirror 612 and focused by lens 606 onto camera 602. In some embodiments 10% of the reflected light is transmitted through mirror 612, although more or less light, such as 1%, may be transmitted. In one embodiment, lens 606 comprises an f=100 L2 lens that produces a spot size on camera 602 of approximately 30 μm and a depth of field of about ±0.3 mm. These numbers, however, are merely exemplary and do not limit the invention in any way.

The focal position 620 of laser beam 632 may be scanned or moved by controlling galvo mirrors 608, zoom beam expander 614, and/or objective 610. Movement of the focal position 620 is illustrated by the arrows adjacent focal position 620, which illustrates that focal position 620 may be scanned horizontally as well as vertically (i.e., may be scanned along orthogonal x, y, and z axes). As mentioned previously, some laser light is reflected back from anatomical feature 604, transmitted through mirror 612, and captured by camera 602. The light captured by camera 602 forms a single spot (i.e., focal spot 662 of FIG. 6B). This may be a conjugated plane. The focal plane of the laser may be changed by changing the scan lens or by other means. The focal plane may change along Z axis, but will usually come back to a focal spot 662 on camera. When the focal position 620 intersects tissue, some light is usually reflected. The reflected light may come to a focus (i.e., focal spot 662) back at the camera and the tissue of anatomical feature 604 at focal position 620 may be imaged (660 of FIG. 6B). The color, shape, and intensity of the spot on camera 602 will vary depending on whether focal position 620 is located at the aqueous humor, the capsule, the lens, and the like (spots 662 and 664 represent different spot shapes, colors, and intensities of imaged light representing various ophthalmic features). In this manner the location of each anatomical feature may be determined or measured and an appropriate therapeutic procedure may be determined and/or applied. A Z encoder signal of objective 610 may provide the depth of the cut in microns. The spot 662 on camera 602 may not move during x and y scanning of the pattern if camera 602 in the focal plane of lens 606.

Mirror 612 may be a partially silvered galvo mirror, or in some embodiments may include a multilayer dielectric stack. Laser light may be reflected back to camera 602 and imaged 660 when the index of refraction of the material at focal position 620 changes, such as when a different material is encountered, a surface of the material is encountered, and the like. As described herein, the focal position 620 may be driven along the optical axis, such as in the 3-6 mm or more range. If a surface interface (e.g. tissue surface interface) is at focal position 620, then a focal spot 662 may be produced on image 660 and captured by camera 602. If a surface interface is not at focal position 620, a slightly enlarged spot 664 may be produced and/or detected. The enlarged spot 664 will generally have a lower total irradiance (e.g. watts per square centimeter), but the same total power. The enlarged spot 664 represents an out of focus spot and indicates that focal position 620 is not at a surface interface of an anatomical feature.

In some embodiments, if the focal position 620 is focused on an optical interface, the back-reflected beam is also focused onto camera 602. The spot size on camera 602 may be about 30 μm. If the focal position 620 is focused above or below the surface, such as by 60 μm, the spot size on camera 602 may be about 60 μm. Such an embodiment may allow depth measurements within an accuracy of about 3-5 μm and may provide an auto-z that compensates for cone height manufacturing errors.

As the focal position 620 is driven, such as from 0 to 6 mm, and more commonly 3 to 6 mm, a sensor (not shown) may indicate the focal position depth. A correlation may be made for the focal position 620 when scanning in x, y, and z directions, for example, each pulse of the laser beam may be correlated with an x, y, and z position. When scanning through a volume, every time a camera frame is obtained (i.e., image 660), it may be possible to know the x, y, and z position of the captured image 660. In this way, detection of a tissue surface (e.g., capsule, lens, cornea, and the like) is possible. The data on the location may be determined, in part, from knowledge of the location of the system and the laser beams focus. In this manner, it is possible to determine the configuration at any point in time. Data for camera frames may be acquired and correlated to where the laser beam is focused (e.g. the query location). Each frame (i.e., image 660) may have an x, y, z location associated with it.

The captured image 660 and corresponding location may be analyzed to detect anatomical features 604 and/or properties of the anatomical feature (e.g., tilt, surface location, depth, and the like). For example, as described herein, bright spot or focal spot 662 may be produced or detected in captured image 660 at a tissue surface at the x, y, and z location. An entire database of captured images 660 may be analyzed to find focal/bright spots 662. The x, y, and z locations corresponding with the focal/bright spots 662 may then be mapped to provide a 3-dimensional image of one or more anatomical features 604 of the eye, such as the capsule, lens, cornea, and the like. Anatomical features 604 may thus be identified and the location and/or orientation of those features may be mapped in 3D space.

If the focal position 620 is positioned on an interface, such as con-glass/air, cone-glass/cornea, cornea/aqueous, aqueous/capsule, and the like, a sharp focal spot 662 may appear on camera 602. The reflectivity of the different interfaces may be approximately: Cone glass/air=3.4%, Cone glass/cornea=0.61%, Cornealaqueous=0.034%, and Aqueous/capsule=0.19%. The depth of the aqueous/capsule interface can be measured as well.

Scanning or imaging the eye in this manner may be done using a helical scan, a raster scan, or any other type or pattern of scan. A helical scan may involve mapping out a cylinder volume of the eye. In some embodiments, a volume of the eye may be scanned according to a predefined pattern, such as a raster or helical scan at a selected pitch. As the volume of the eye is scanned, focal/bright spots 662 corresponding to tissue surfaces may be detected. As tissue surfaces are detected throughout the scanned volume, tissue shapes may be determined or calculated and measured. Thus, various anatomical features 604 of the eye may be detected and measured. Scanning and imaging or mapping anatomical features 604 of the eye may be performed at a low power or scanning energy level, as previously discussed hereinabove, based on the operating laser spot size and pulse width and the specific ocular tissue being scanned, imaged, or mapped.

In some embodiments, a fluorescence effect of the tissue of anatomical feature 604 at focal position 620 may also be obtained instead of or in addition to the reflected image 660 captured by camera 602. To obtain a fluorescence effect, the optical system may need to be corrected for color change. If the scanning/measurement process is based on fluorescence, the optical system may need adjusting based on laser wavelength and/or fluorescence wavelength.

Using the optical system and femtosecond laser described herein to range find (i.e., scan and map) anatomical features of the eye may ensure that delivered therapeutic laser energy remains away from the cornea. For example, the location and orientation of the lens may be determined so that ablation energy from the femtosecond laser can be delivered to the lens to remove and/or disrupt it. The optical system may deliver ablation energy during a therapeutic treatment concurrent with or closely after range finding (i.e., a scanning and mapping operation). For example, an anatomical feature (e.g., lens) may be located and measured to determine the orientation and depth, and then ablation energy may be delivered to the anatomical feature. Delivering ablation energy may involve increasing the energy level of the scanning laser to a therapeutic level. Alternatively or additionally, other scans may be possible, for example changing the shape and/or orientation of the anatomical feature, increasing the laser beam energy, and performing a capsulorhexis scan.

In some embodiments, the location of the changes to the optical system may be determined. For example, there may be changes concentrated in the 6× beam expander, to obtain an additional 3-6 mm of depth. The scanning procedures described herein may be performed with laser beam intensities that do not cause optical damage to the cone glass. Similarly, depth measurements of the capsule may be taken without causing optical damage to the capsule.

Figure 7:
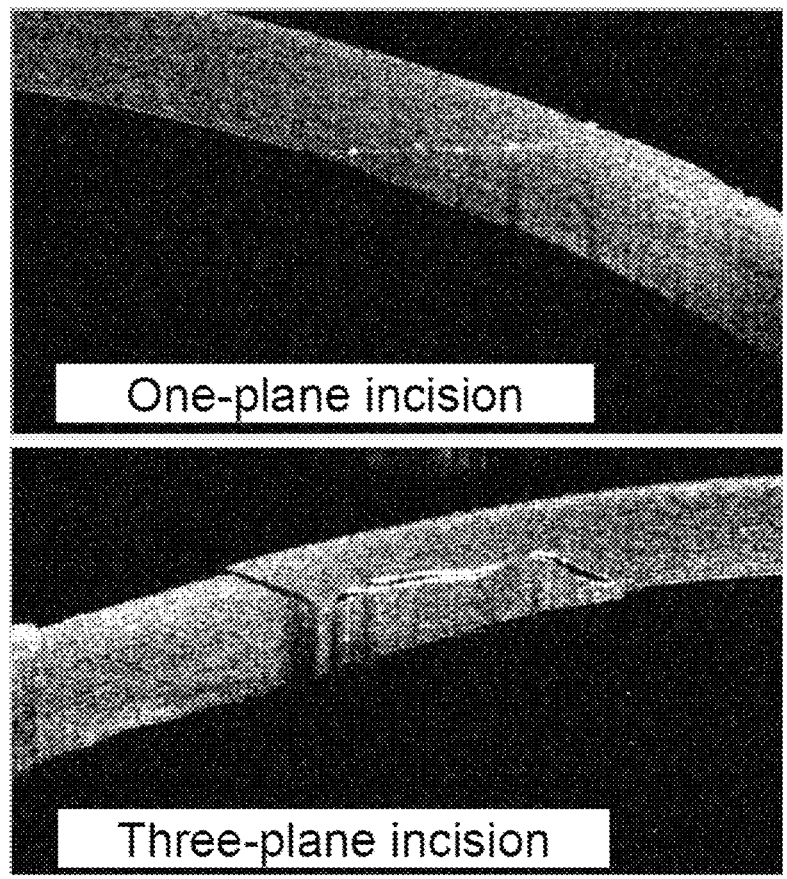
FIG. 7 illustrates incisions of the cornea that may be made by the optical systems described herein according to one embodiment of the present invention.

In some cases, the optical system can be used for flap cutting in addition to range finding/diagnostic scanning (i.e., anatomical imaging and mapping) and therapeutic treatment (e.g., capsulorhexis, capsulotomy, and/or lens fragmentation). For example, FIG. 7 illustrates the femtosecond laser (or other laser) of the optical system being used to incise the cornea to cut a flap. The femtosecond laser may be used to make arcuate or other incisions in the cornea, which incisions may be customized, intrastromal, stable, predictable, and the like. Likewise, corneal entry incisions may be made, which are custom, multi-plane, and self-sealing. In addition, the optical system described herein may be used to provide laser cataract surgery in the cornea. Such procedures may be provided using the flexibility of incisional software and range finding. The optical system may be used for precision locating of the anterior corneal surface with a hard or liquid interface.

In some embodiments, the optical system may be used to provide a secondary check, such as to obtain a finer resolution on anatomical feature surface depths by comparing spot sizes of different images (e.g., before and after signals). Similarly, comparing spot sizes of different images (e.g., before and after signals) may increase resolution of the image. For example, a 5× increase in resolution may be possible.

Figure 12:
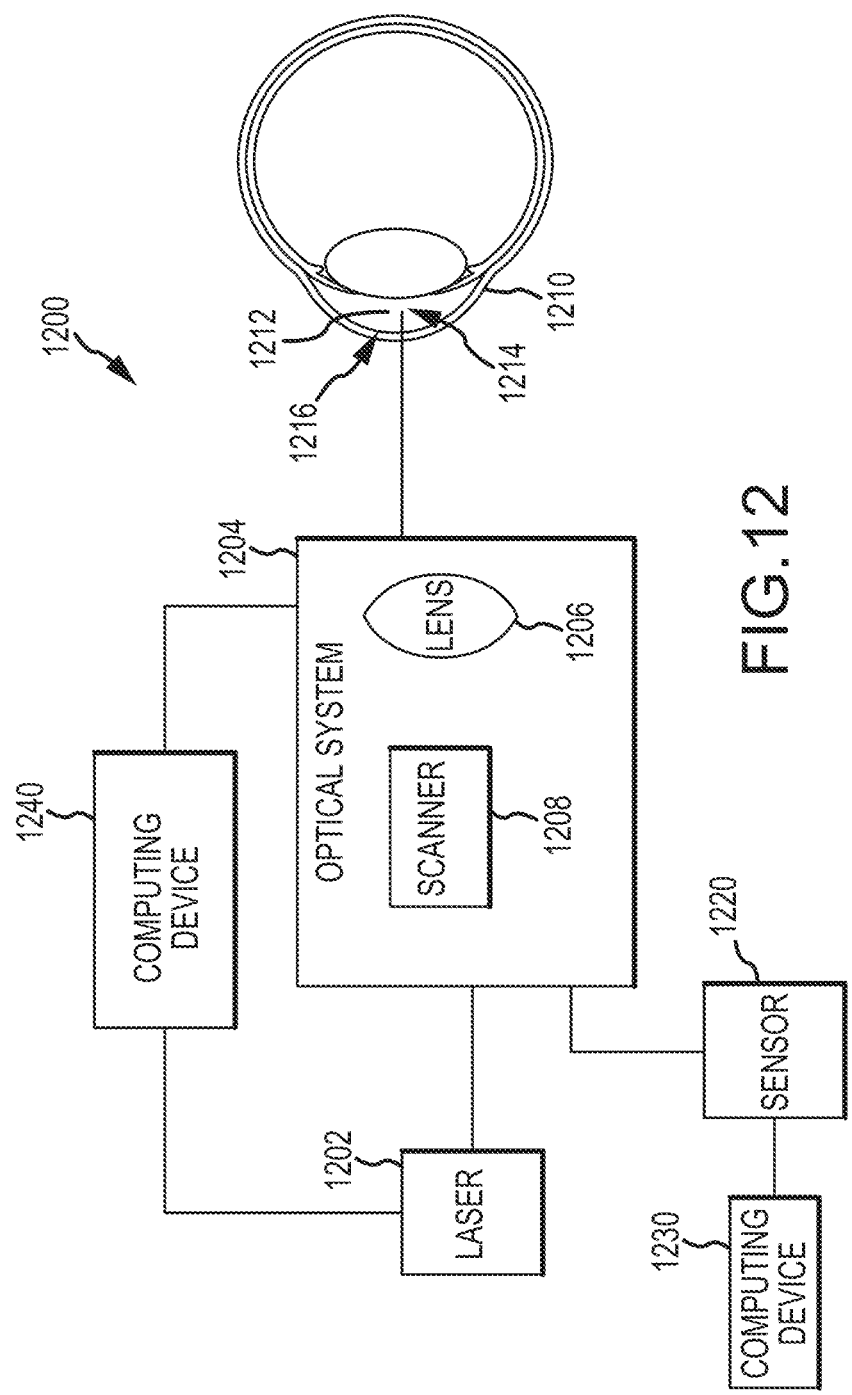
FIG. 12 illustrates a system for treating an eye of a patient according to one embodiment of the present invention.

Referring now to FIG. 12 illustrated is a system 1200 for treating an eye 1210 of a patient. The eye 1210 includes a fluid posterior to a cornea. System 1200 includes a femtosecond laser 1202 configured for directing femtosecond energy along a path. System 1200 also include an optical system 1204 disposed along the path from the laser. Optical system 1204 includes a focusing lens 1206 and a scanner 1208 so as to scan a focus 1212 of the femtosecond energy along a path within the patient's eye 1210. The path may extend posterior to the patient's cornea within the fluid so that the path includes a first location 1214 disposed within a tissue of the eye and a second location 1216 disposed within the cornea. In some embodiments, the focus 1212 imparts a sufficient amount of energy to the particular tissue of the eye 1210 such that a plasma is generated. For example, the femtosecond energy imparted to the particular tissue of the eye 1210 at the focus 1212 is sufficient for photodisruption of the same tissue. In other embodiments, the femtosecond energy imparted to the particular tissue or fluid of the eye 1210 at the focus 1212 is less than the plasma generation threshold corresponding to the same tissue or fluid. For example, as previously mentioned hereinabove, the femtosecond energy may be less than the plasma generation threshold photodisruption threshold for the specific ocular tissue or fluid, or less than the energy threshold for bubble formation in the specific ocular tissue or fluid, or at a fraction of the energy threshold for bubble formation in the specific ocular tissue or fluid.

System 1200 also includes a sensor 1220 oriented along the path so as to sense a first signal associated with a first focus location 1214 within the eye 1210 and a second signal associated with a second focus location 1216 within the eye 1210. System 1200 further includes a computing device 1230 communicatively coupled with the sensor 1220. The computing device determines a location of an interface between the fluid and a tissue of the eye 1210 in response to the first signal and the second signal. System 1200 may also include an additional computing device 1240 communicatively coupled with the femtosecond laser 1202 and/or optical system 1204. Computing device 1240 may control laser 1202 and/or optical system 1204 by transmitting signals to those devices. Computing device 1240 may also receive feedback from laser 1202 and/or optical system 1204. In some embodiments, computing device 1230 and computing device 1240 comprise the same device.

Applanation Lens

Figure 8:
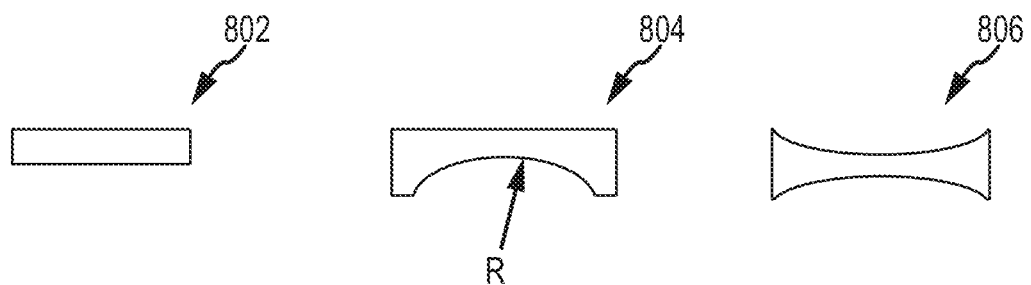
FIG. 8 illustrates various applanation lenses that may be used according to embodiments of the present invention.

An applanation lens may be used with the optical system to stabilize the eye during a diagnostic or therapeutic procedure and/or to correct for one or more aberrations, such as astigmatism. FIG. 8 illustrates exemplary applanation lenses that may be used with embodiments of the invention. Applanation lenses may be placed on the exterior surface of the cornea during a diagnostic or therapeutic procedure. In one embodiment, the applanation lens may be a flat lens 802, with planar top and bottom surfaces. In another embodiment, the applanation lens may include a planar top surface and a curved bottom surface 804. In yet another embodiment, the applanation lens may include curved top and bottom surfaces 806. The curvature of one or more of the surfaces may comprise a radius R, which in one embodiment may be between 120 and 130 mm, and more commonly about 124 mm.

Applanation lens 806 may be used to correct an aberration, such as astigmatism. Astigmatism may not be noticed on axis, but may be noticed in field. The curvature of applanation lens 806 may balance the astigmatism. Such aberration correction may be important when cutting rings or arcuate incisions with the optical system. After the applanation lens is placed atop the cornea, the diagnostic scan procedures described herein may be used to measure beam spot size/dimensions so as to provide an indication of any wrinkling that may occur due to applanation of the cornea. A similar procedure may be performed after an intraocular lens (IOL) is placed in the capsular bag to determine if the new lens is wrinkled. The scanning procedure may also be performed to detect one or more of the following conditions: curvature of the patient interface contact surface after the applanation lens is applied (e.g., the cornea curvature may be determined after the applanation lens is applied); bubbles that might be present at the meniscus formed by the contact surface of the patient interface and the cornea; apex and/or vertex location of the contact surface of the patient interface.

In other embodiments, the applanation lens may be positioned in fluid communication with the cornea, such as to reduce intraocular pressure that may be result from applanation. For example, U.S. patent application Ser. No.

13/230,590, the disclosure of which is incorporated herein by reference, describes the use of an applanation lens that is positioned proximal to but not contacting the corneal surface. A liquid may be disposed between the applanation lens and the cornea. Alternatively, instead of using an applanation lens, one or more components of the optical system could adjust to compensate for the astigmatism. This may be specific to systems being looked at for capsulorhexis, but not specific to a particular laser system.

In some embodiments, the scanning/measurement process is performed with a conjugate system. The indication of a surface is performed with a therapeutic femtosecond laser beam, although in other embodiments, a separate detection sensing beam may be used. The therapeutic femtosecond laser beam may be operated at lower non-therapeutic energy levels.

The diagnostic scan procedures and/or therapeutic procedures described herein may be combined with other diagnostic techniques such as optical coherence tomography (OCT) to determine a patient's ophthalmic anatomy prior to a therapeutic treatment. Similarly, the diagnostic scan procedures described here may be used for pachymetry prior to LASIK or other procedures.

Exemplary Therapeutic and/or Diagnostic Procedures

Figure 9:
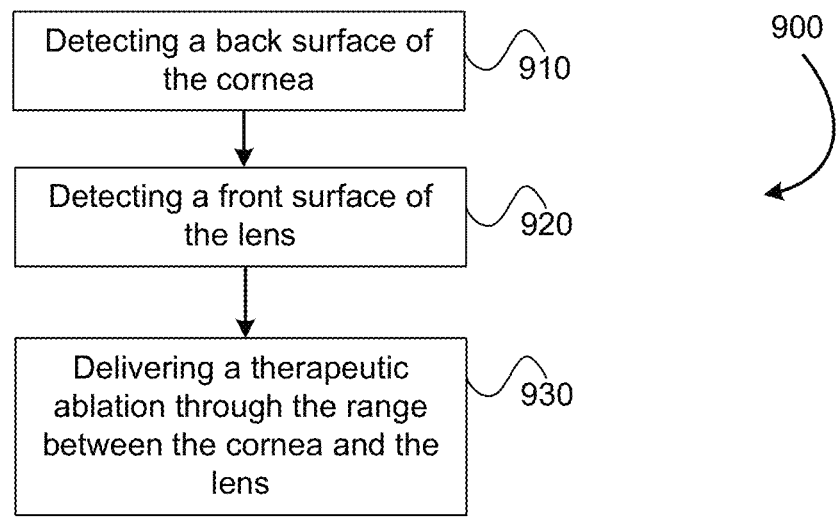
FIG. 9 illustrates a method for providing capsulorhexis treatment according to one embodiment of the present invention.

FIG. 9 illustrates a method 900 for providing capsulorhexis treatment. At block 910, a back surface of the cornea is detected via a diagnostic scan using a femtosecond laser of the optical system. A small gap may be provided for a safety zone. At block 920, a front surface or interface of the lens is detected via the diagnostic scan. At block 930, a therapeutic ablation is delivered through the range between the cornea and the lens via a therapeutic scan. Alternatively or additionally, the front and back surface of the capsule may be detected during the diagnostic scan and the therapeutic ablation may be delivered between this range or a portion thereof. As described herein, the diagnostic and therapeutic scans may be delivered via the femtosecond laser of the optical system. In delivering the scans, the femtosecond laser may be adjusted between a diagnostic/scanning energy level and a therapeutic energy level.

Another method may involve detecting the cornea and calculating a safe scanning/therapeutic distance by determining an absence of signal as the depth of the laser beam focal position is adjusted away from the cornea. In other words, a safe distance to begin therapeutic treatment may involve determining that a therapeutic starting point is sufficiently far from the cornea. The method may also involve scanning through a range of a couple of millimeters or more to determine a minimum and maximum height of the lens. If nothing else is detected in that range, then therapeutic treatment may proceed.

Figure 10:
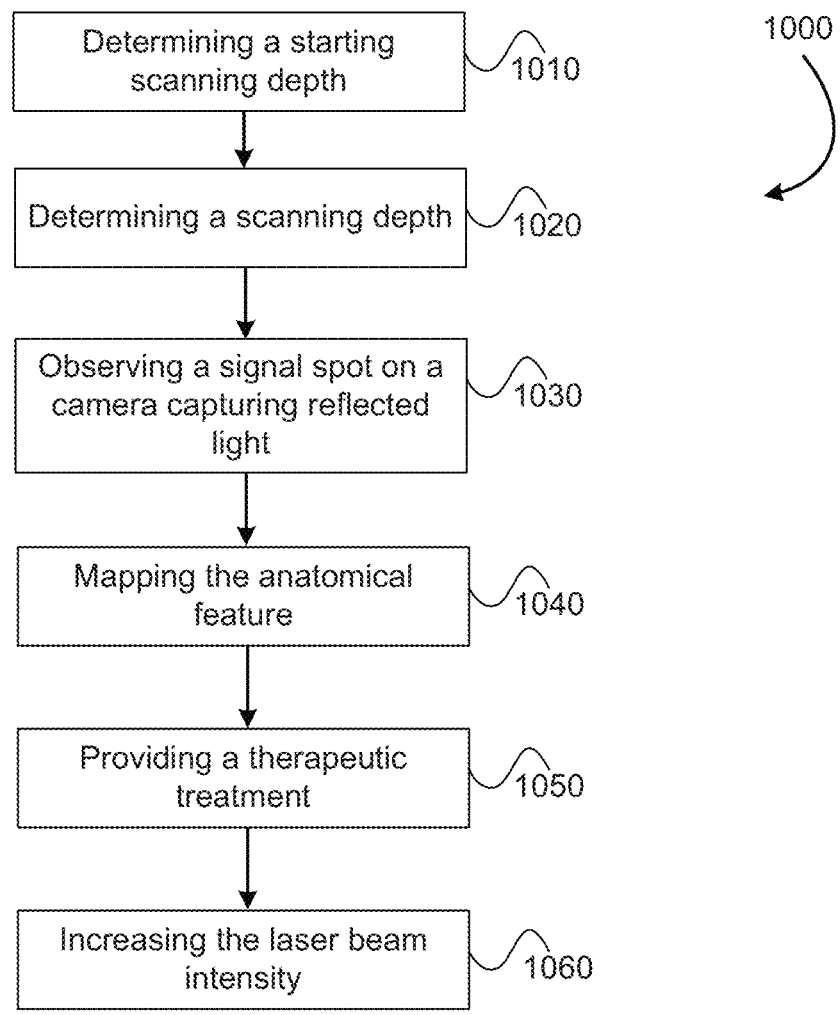
FIG. 10 illustrates a method for detecting and/or providing therapeutic treatment to an anatomical feature with an optical system according to one embodiment of the present invention.

FIG. 10 illustrates a method for detecting and/or providing therapeutic treatment to an anatomical feature (e.g., capsule, lens, and the like) with an optical system and/or femtosecond laser. At block 1010, a starting scanning depth may be determined. The starting scanning depth may be about 3 mm from the cornea. At block 1020, a scanning depth is determined. The scanning depth represents the depth the focal position of the laser beam will traverse. In one embodiment, the scanning depth is between 0-6 mm, between 3-6 mm, and the like, although other depths are possible. The scanning depth is typically a depth where the location of the capsule, lens, and the like is expected.

At block 1030, a signal spot or light intensity on a camera capturing reflected light is observed to determine a light intensity increase of the signal spot. The light intensity increase represents when the focal point of the laser beam encounters the capsule. If the lens is tilted with respect to the optical axis of the objective or is de-centered, the signal spot may appear or disappear depending on the position of the laser beam's focal point. If the laser beam's focal point is in aqueous areas the signal spot intensity may be low. Similarly, when the laser beam's focal point encounters the lens or is positioned thereon, the signal spot intensity may be high. At block 1040, the anatomical feature may be mapped by scanning the laser beam's focal point and observing the signal spot to determine if the focal point is positioned on or near the anatomical feature (e.g., lens) or on another anatomical feature (e.g., capsule, aqueous area, and the like).

At block 1050, a therapeutic treatment may be provided by calculating a vertical (or horizontal) sidecut and inputting the vertical sidecut into a control system. In one embodiment, the vertical sidecut may be roughly 5-6 mm in diameter. At block 1060, the laser beam intensity may be increased (e.g., to a therapeutic level) and the laser beam's focal point may be scanned in accordance with the vertical sidecut.

The vertical step size of scanning/therapeutic procedure can be variable. For example, the step size may initially be 10 μm. When an anatomical feature surface is encountered, the step size may be adjusted to 2 μm. The scanning and/or therapeutic step may continue with the 2 μm step size until the anatomical feature is mapped and/or treated.

In some embodiments, the diagnostic scan may be combined with the therapeutic treatment. For example, when an anatomical feature (e.g., capsule) to be treated is encountered, the laser beam intensity may be adjusted to a therapeutic level. The laser beam focus may be adjusted vertically and/or horizontally to provide the desired therapy and the signal spot may be monitored to determine when the laser beam focus encounters an edge of the anatomical feature and/or when an additional anatomical feature is encountered.

Figure 11:
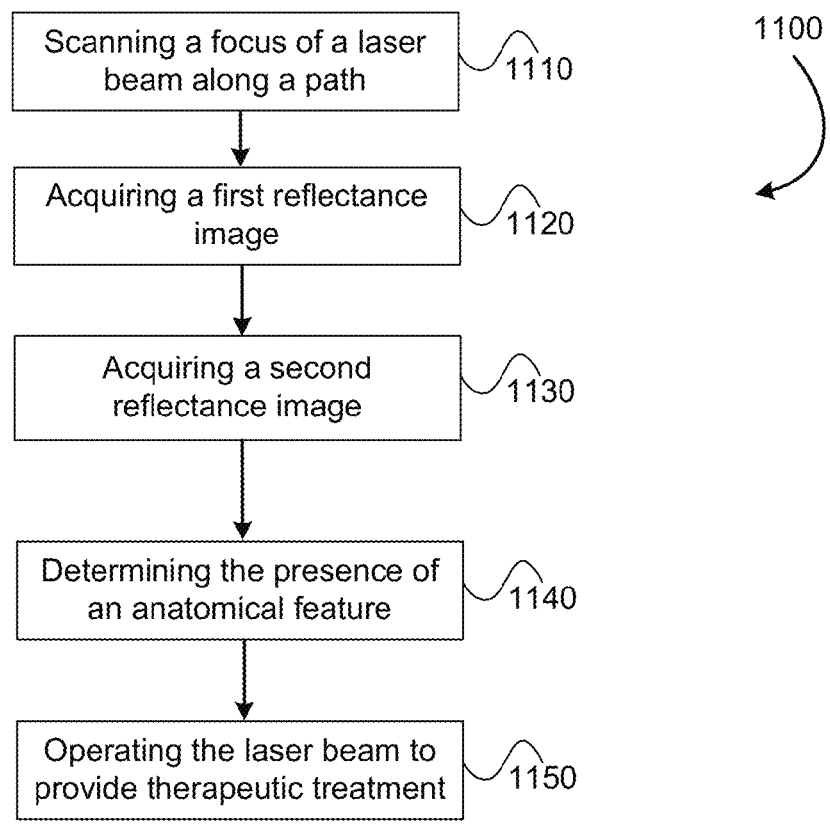
FIG. 11 illustrates a method for analyzing the ophthalmic anatomy of a patient posterior to the cornea and/or for providing therapeutic treatment to the ophthalmic anatomy according to one embodiment of the present invention.

FIG. 11 illustrates a method for analyzing the ophthalmic anatomy of a patient posterior to the cornea and/or for providing therapeutic treatment to the ophthalmic anatomy. At block 1110, a focus of a femtosecond laser beam is scanned along a path within the patient's eye. A portion of the path may be disposed posterior to the patient's cornea and the path may include a first location and a second location. At block 1120, a first reflectance image is acquired. The first reflectance image may be associated with the focus disposed at the first location. At block 1130, a second reflectance image is acquired. The second reflectance image may be associated with the focus disposed at the second location. At block 1140, the presence or absence of an ophthalmic anatomical feature of the eye may be determined based on a comparison between the first reflectance image and the second reflectance image. At block 1150, the femtosecond laser beam may be operated to provide therapeutic treatment to one or more areas of the anatomical features. The anatomical feature may include a capsular bag and/or a lens within the capsular bag. The therapeutic treatment provided by the laser (e.g., the femtosecond laser) may include disrupting a capsule or lens and may include lens fragmentation, capsulorhexis, and/or capsulotomy. The femtosecond laser may be operated at a lower energy level during the scanning process and may be operated at a higher energy level to provide the therapeutic treatment. Although the embodiment of FIG. 11, and other embodiments described herein, refers to first and second locations, it should be realized that the diagnostic and/or therapeutic scans may include multiple other locations (e.g., $3^{rd}$, $4^{th}$, $5^{th}$, . . . , $n^{th}$, etc.) depending on the scan pattern, scan parameters, anatomical feature, diagnostic and/or therapeutic procedure, and the like. For example, a diagnostic scan may involve 2D or 3D mapping of one or more surfaces of an anatomical feature, which may involve multiple thousand scan locations at various locations within two dimensional or three dimensional spaces. Likewise, a therapeutic scan may involve multiple thousand scan locations corresponding to various anatomical features of the eye.

Examples

Using the range finding and/or therapeutic treatments described herein, a continuous curvilinear capsulorhexis (CCC) was performed using a modified, extended focal range femtosecond laser, such as the iFS laser manufactured by Abbott Medical Optics Inc., to locate the surface of the capsule bag and to perform capsulotomy in cadaver eyes ex-vivo and in rabbits in-vivo. Results demonstrated improved effectiveness of the femtosecond laser in exact placement, precise sizing, and positioning of the anterior capsulotomy.

The cadaver procedure involved using 27 human cadaver globes (corneas intact or removed) to evaluate the femtosecond laser-assisted CCC treatments. The cadaver globes were measured using a PalmScan handheld pachymeter (Micro Medical Devices) to determine corneal thickness and anterior chamber depth prior to femtosecond laser scanning and treatment. The eyes were inspected under a surgical microscope for ease of capsular tissue removal, circularity of the capsulotomy, and capsular bag integrity.

Pre-capsulotomy measurement of the anterior chamber depth (ACD) was performed with a modified femtosecond laser-guided range-finding feature with a standard deviation of approximately 0.87 μm. Table 1 below provides some data of this process.

TABLE 1

Results of cadaver tissue for comparative analysis of biometry vs. range finding with average percent error converted to microns (0.075 μm)

| Palm scan | Range finding | % Error normalized |
|---|---|---|
| 2.54 | 3.30 | 19.82 |
| 2.52 | 2.36 | −26.00 |
| 3.68 | 4.08 | −5.02 |
| 3.81 | 4.50 | 1.66 |
| 3.81 | 4.43 | 3.04 |
| 4.64 | 4.52 | −0.99 |
| Ave % error converted to microns | | 0.075 μm |

The globes tested without corneas had 100% separation at 0.6 μJ energy, similar to recent clinical studies. As shown in Table 2 below, the capsulotomy tissue removed ranged from 2.5-6 mm in diameter with greater than 75% complete separation on all eyes. Calibrated laser settings were used. All tissue removed was round and had smooth edges.

TABLE 2

Results of cadaver tissue size and associated completeness of separation

| Diameter | % Complete separation |
|---|---|
| 6.0 mm | 75% |
| 5.0 mm | 90-100% |
| 4.5 mm | 95% |
| 3.5 mm | 100% |
| 3.0 mm | 80-100% |
| 2.5 mm | 100% |

Figure 13:
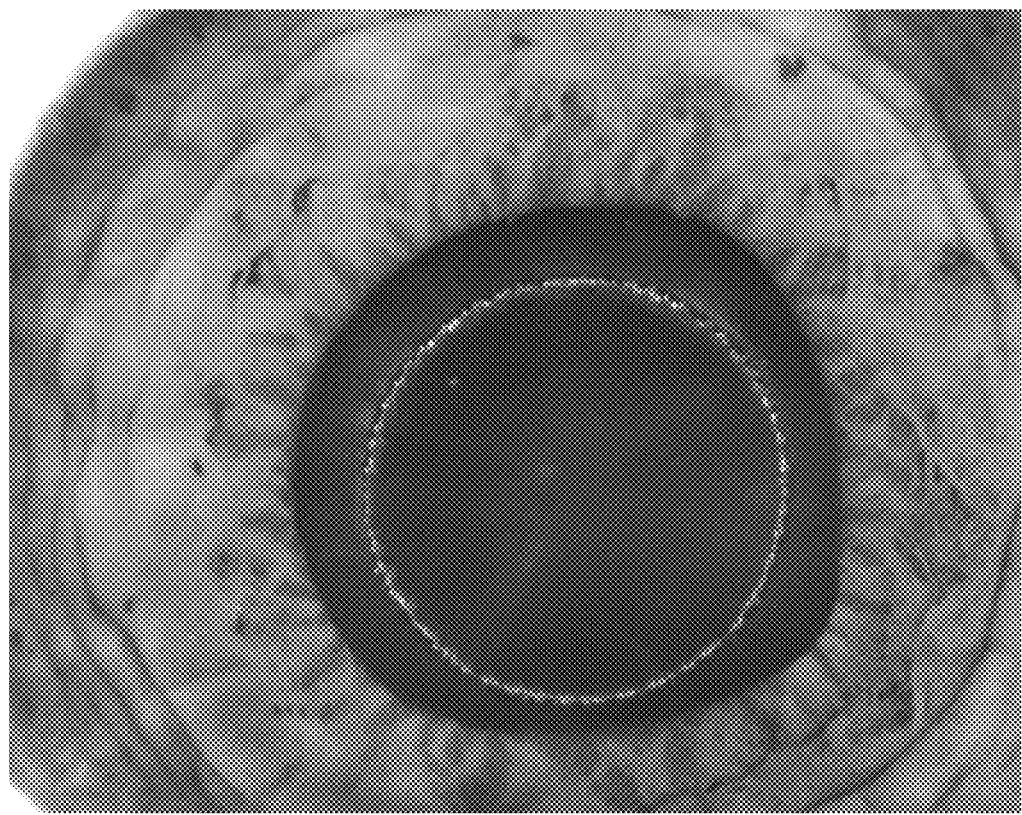
FIG. 13 illustrates a representative image of the placement, centration, and uniform circularity of a laser-assisted capsulotomy relative to the pupil in a cadaver eye according to one embodiment of the present invention.

A representative image of the precise placement, centration, and uniform circularity of the femtosecond laser-assisted capsulotomy relative to the pupil in a cadaver eye immediately following treatment is provided in FIG. 13.

Figure 14A:
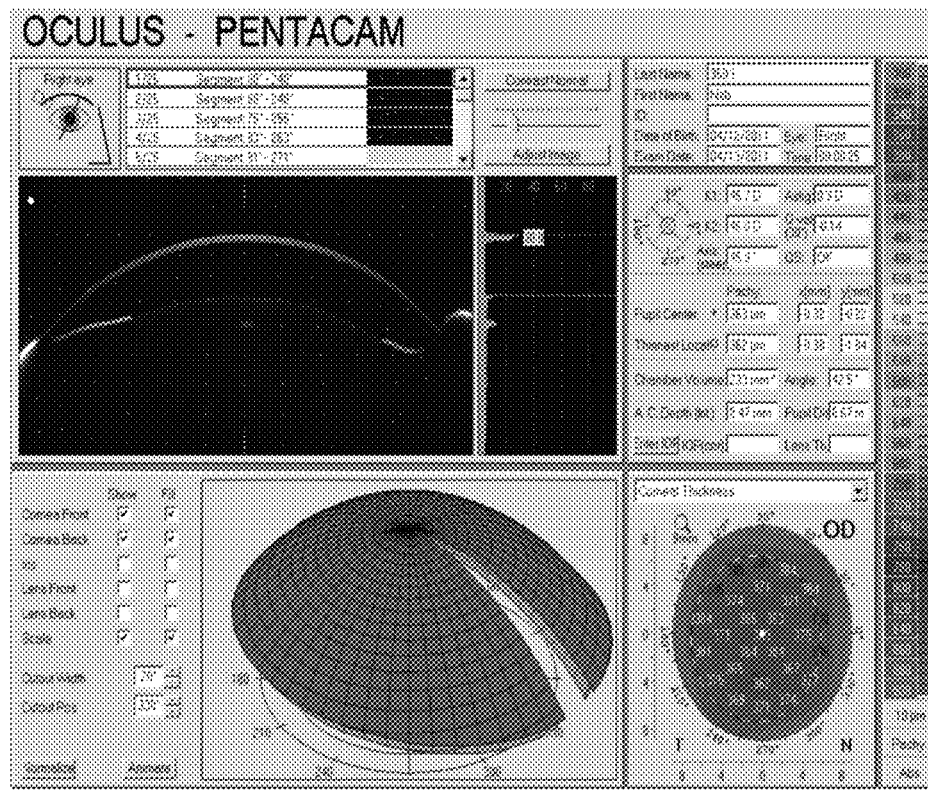
FIG. 14A illustrates a screen shot of a system used to measure the corneal pachymetry and anterior chamber depth of a rabbit eye according to one embodiment of the present invention.

An in vivo rabbit procedure was performed using 18 New Zealand White rabbits (average weight approximately 3.27 kg) that underwent femtosecond laser-assisted CCC treatment in the right eye and manual capsulorhexis in the left eye. The corneal pachymetry (thickness) and anterior chamber depth of the rabbit eyes were measured pre-operatively using a Pentacam HR Scheimpflug camera (Oculus) as shown in FIG. 14A. Immediately following the femtosecond laser scanning and treatment procedure the ease of capsular tissue removal, circularity of the capsulotomy, and capsular bag integrity were assessed. Postoperative ocular healing response, including stability of the capsular bag after IOL implantation, was monitored from 1-3 months by slit-lamp biomicroscopy (see FIG. 14C).

Figure 14B:
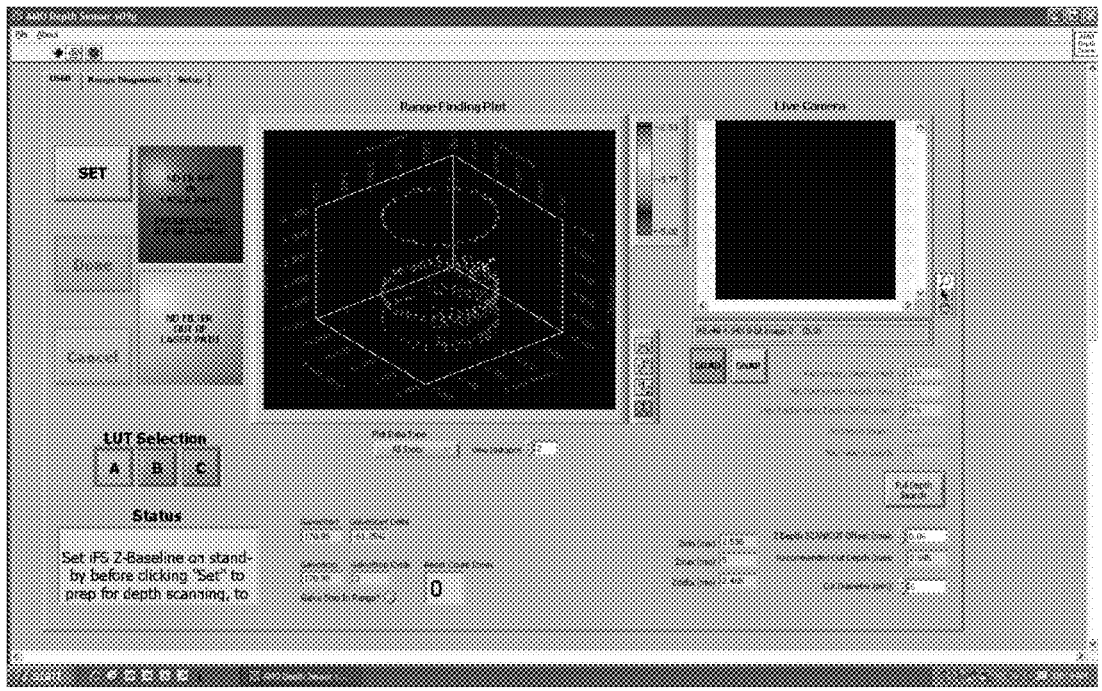
FIG. 14B illustrates a screen shot of a range-finding scan through the corneal surface, lens surface, and internal structure of a lens according to one embodiment of the present invention.

A preoperative comparison of biometry versus the range finding depth measurements was performed. The range-finding process scans yielded precise depth positions using the laser at ultra-low energy, such as those described herein. Machine vision captured the reflected beam's sharpest images to determine the position and tilt of the anterior capsule surface, similar to the range finding processes described herein. A representative image of the range-finding scan through the corneal surface, lens surface, and internal structure of the lens is provided in FIG. 14B.

The biometry data for pachymetry was correlated with the range-finding data to predict the depth for laser treatment patterns. As shown in Table 3 below, the normalized average error between the two data sets was about −0.52%.

TABLE 3

Results of in vivo rabbit biometry vs. range finding normalized data

| Pentacam AC depth\pach | Range finding (mm) | | Difference PC vs. RF min (mm) | Difference normalized (mm) | Normalized error | % Error normalized |
|---|---|---|---|---|---|---|
| | Min | Max | | | | |
| 2.907 | 3.83 | 3.94 | −0.923 | 3.171 | 0.264 | 0.08 |
| 2.863 | 3.58 | 3.70 | −0.717 | 2.921 | 0.058 | 0.02 |
| 2.900 | 3.52 | 3.64 | −0.620 | 2.861 | −0.039 | −0.01 |

TABLE 3-continued

Results of in vivo rabbit biometry vs. range finding normalized data

| Pentacam AC depth\pach | Range finding (mm) Min | Range finding (mm) Max | Difference PC vs. RF min (mm) | Difference normalized (mm) | Normalized error | % Error normalized |
|---|---|---|---|---|---|---|
| 2.944 | 3.65 | 3.80 | −0.706 | 2.991 | 0.047 | 0.02 |
| 2.956 | 3.68 | 3.79 | −0.724 | 3.021 | 0.065 | 0.02 |
| 2.896 | 3.16 | 3.32 | −0.264 | 2.501 | −0.395 | −0.16 |
| SD min RF | 0.226 | | Ave of diff −0.659 | | | Ave % error −0.52% |

Post treatment capsular size data for 6 rabbit eyes was obtained after 1 day and 1 week. The capsulotomy size change over the 1 week post-operative time frame was measured via Adobe® Pixel count and showed that the standard deviation of average change in capsulotomy size was 42 μm or less. Right eyes (OD) had laser capsulotomy treatments while Left eyes (OS) had manual capsulorhexii. Data results are provided in Table 4 below.

TABLE 4

Results of in vivo rabbit capsular opening slit lamp image capture and measurement at 1 day and 1 week.

| | OD | | | | OS | | | |
|---|---|---|---|---|---|---|---|---|
| | Size, day one | | Size, week one | | Size, day one | | Size, week one | |
| | Vert | Horiz | Vert | Horiz | Vert | Horiz | Vert | Horiz |
| | 5.19 | 5.62 | 5.01 | 5.38 | 3.95 | 5.18 | 3.94 | 4.7 |
| | 5.36 | 5.63 | 5.25 | 5.5 | 3.72 | 4.29 | 3.43 | 4.1 |
| | 5.13 | 5.71 | 4.18 | 4.45 | 3.99 | 4.80 | 3.86 | 4.43 |
| | 5.03 | 5.52 | 5.07 | 5.33 | 4.16 | 4.28 | 4.1 | 4.41 |
| | 4.91 | 5.64 | 5.16 | 5.48 | 4.37 | 4.59 | 4.4 | 5.04 |
| | 4.77 | 5.36 | 4.96 | 5.54 | 3.63 | 4.17 | 3.26 | 3.87 |
| Average | 5.07 | 5.58 | 4.94 | 5.28 | 3.97 | 4.55 | 3.83 | 4.43 |
| SD | 0.21 | 0.12 | 0.39 | 0.41 | 0.27 | 0.39 | 0.42 | 0.42 |

Figure 14C:
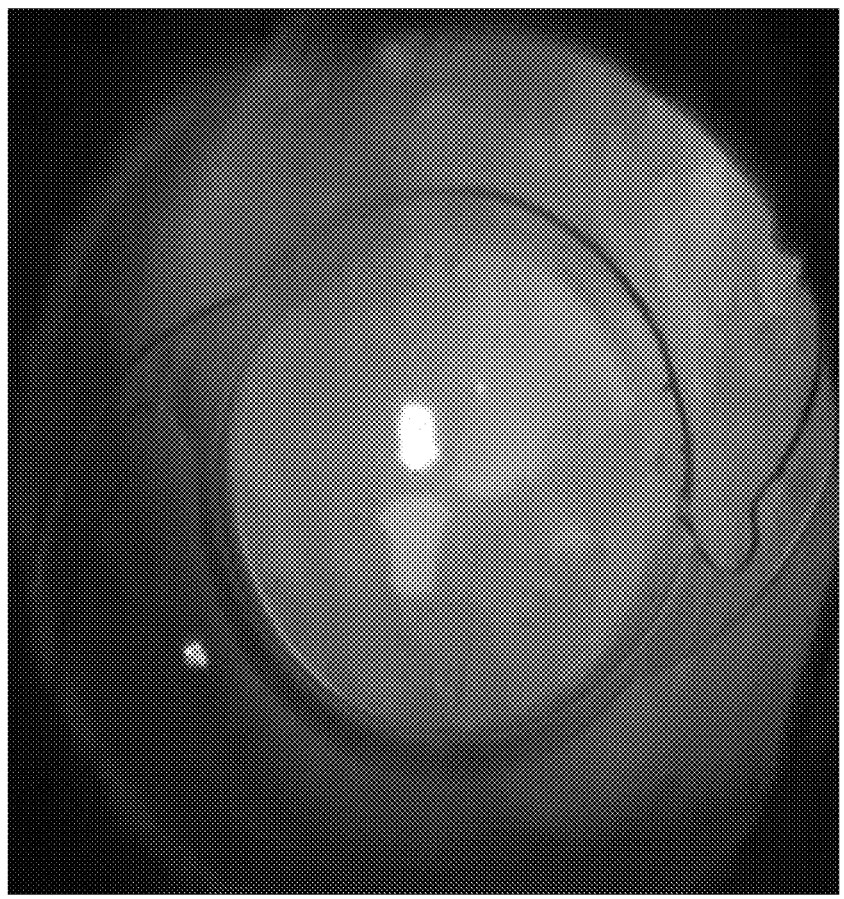
FIG. 14C illustrates an image of a treated rabbit eye and an intraocular lens implant according to one embodiment of the present invention.

A representative image of a treated rabbit eye showing the accuracy of the femtosecond laser-assisted capsulotomy placement, centration, and uniform circularity over the intraocular lens implant at 1 month post-operative is provided in FIG. 14C.

The above described study shows that the femtosecond lasers described herein are capable of precisely controlled capsulotomy. The femtosecond laser-assisted capsulotomy depth accuracy is repeatable and precise as demonstrated by the comparative analysis of biometry data with average normalized percent accuracy error of −0.52 percent. The in vivo studies demonstrated that the SD of average change in capsulotomy size over one week was 42 μm or less. The ex-vivo and in-vivo studies also demonstrated excellent surgical performance of the femtosecond laser-assisted capsulotomy with respect to lens capsule integrity and stability following capsulotomy and IOL implantation. Accordingly, the femtosecond lasers and/or treatment methods described herein and used in the above described study offer improved treatment capability, accuracy, and precision over manual cataract surgery techniques.

Exemplary Field Upgrade Unit

As mentioned previously, the therapeutic and/or diagnostic scanning procedures described herein may be provided in a field upgrade unit that may be removably coupled with pre-existing laser optical systems. In a non-limiting embodiment, a field upgrade unit was fitted with a corneal femtosecond laser workstations to adapt the workstation to perform laser capsulotomy. The field upgrade unit, and several experimental procedures involving the field upgrade unit, is described below. The field upgrade unit allowed the pre-existing laser optical system to perform the following functions: locate the anterior lens capsule, extend the focus range of the pre-existing laser optical system to reach the capsule, ensure that the energy density at the focus is above the cut threshold, ensure that laser irradiance at the retina is below ANSI limits, ensure that the existing corneal functions remain intact, and the like.

Figure 15:
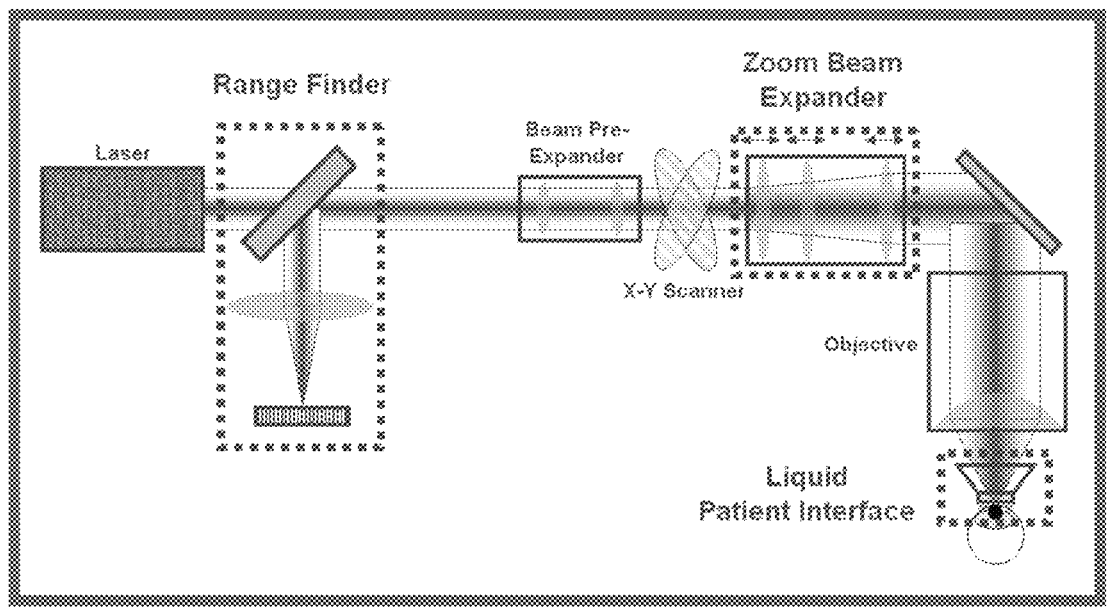
FIG. 15 illustrates an adapted optical system according to one embodiment of the present invention.

To adapt the pre-existing laser optical system to the therapeutic and/or diagnostic scanning procedures described herein (e.g., laser capsulotomy and the like), the pre-existing laser optical system was implemented with the described range finder and zoom beam expander (ZBX). In one embodiment, several corneal workstations were upgraded as well and/or the laser optical system's existing patient interface (PI) was utilized in a unique way to form a liquid interface. The feasibility of the adapted optical systems was then analyzed via computational modeling, measurements, tests with ex-vivo and in-vivo eyes, and human clinical study. An embodiment of an adapted optical system is shown in FIG. 15. As shown in FIG. 15, modifications to pre-existing optical systems that may allow the pre-existing systems to perform the described therapeutic and/or diagnostic scanning procedures (e.g., capsulotomy and the like) may include implementing the described range finder, Zoom Beam Expander (ZBX), and/or the liquid Patient Interface (PI). These components are all shown in FIG. 15 by dashed lines.

The range finder implemented with the pre-existing optical system was designed to image the focus of the surgical beam based on the reflectivity of the third Purkinje image PIII, which is approximately 0.016%. During range finding, the pulse energy was set below the optical breakdown (OB) threshold energy as determined by the onset of bubble formation in water. The capsule depth was determined by imaging the laser focus onto a CCD camera as the laser focus was scanned through the capsule. The accuracy, which depends on the Rayleigh range of the focus, was verified to be within ±20 μm. Because the laser beam of the above described adapted optical system is used for both measurement and surgical purposes, this design substantially reduces or eliminates the risk of registration error between the surgical laser and a separate measurement.

The Zoom Beam Expander (ZBX) implemented in the pre-existing optical system was designed to replace the original fixed beam expander. The ZBX may use the same set of lenses as the original fixed beam expander, thus ensuring the same or similar optical prescription when the system is run in the corneal workstation mode. The focal depth range with the ZBX may be extended from a range of 0 mm to 1.2 mm (the approximate range of original fixed beam expander) to about 0 mm to about 7.0 mm. This range meets the laser capsulotomy needs for approximately 99% of cataractous eyes, which typically have anterior chamber depths in the range of about 2.0 mm to about 4.0 mm.

In experimental studies involving no cornea, the energy sufficient for capsule cutting was measured at about 3 to 4 times the OB threshold energy at the corresponding depth in water. With this design, the high numerical aperture (NA) of the pre-existing optical system may be preserved, which may ensure low threshold energy ($\sim 1/NA2$) for capsulotomy, high sensitivity ($\sim 1/NA2$) for range finding, and/or low peak irradiance at retina ($\sim 1/NA4$). A simulated 4-year cycling of key components was performed to assess the reliability of the adapted optical systems for both corneal and capsulotomy functions. The measured result was a change of less than 2 µm variation in focal depth with no trend. At the system level, a simulation of 1-year ZBX cycling was performed to determine system performance at flap creation conditions.

Figure 16:
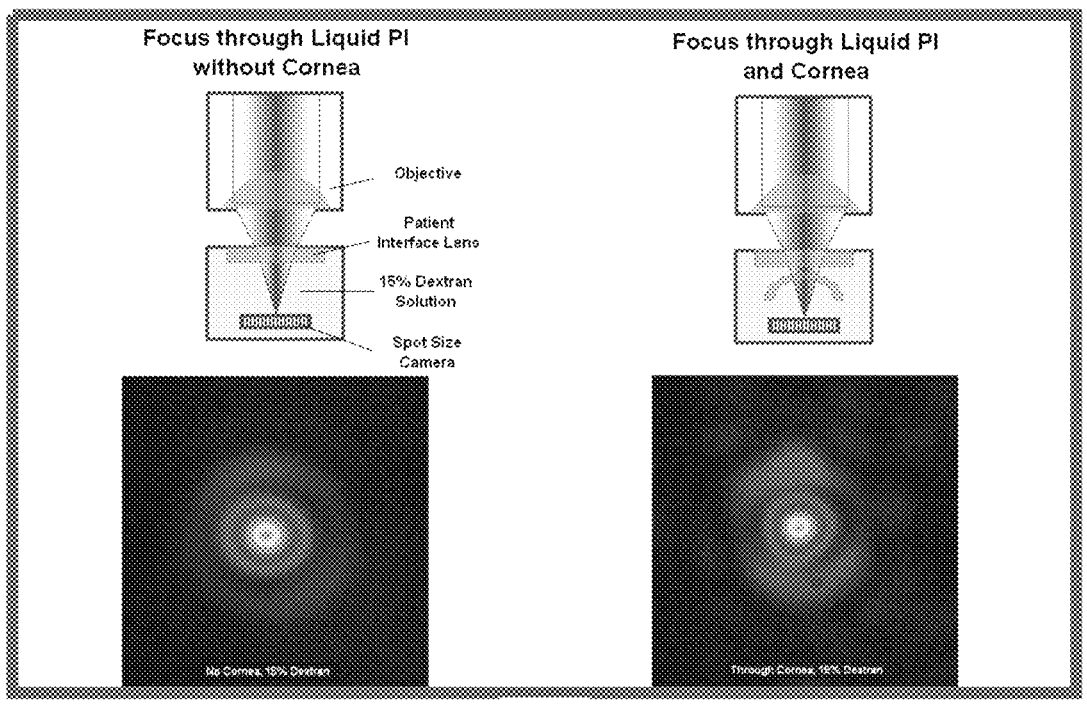
FIG. 16 illustrates a focal quality of a beam passing through a liquid patient interface with no cornea and with a cadaver cornea according to one embodiment of the present invention.

As briefly described herein, the patient interface (PI) can affect the focal quality by deforming the cornea and introducing wrinkles on the posterior surface. A liquid PI can minimize this effect. The focal quality of a beam passing through a liquid PI with no cornea and with a cadaver cornea is shown in FIG. 16. As shown, the cornea may introduce changes to the focus, but the basic beam profile may be well maintained.

Figure 17:
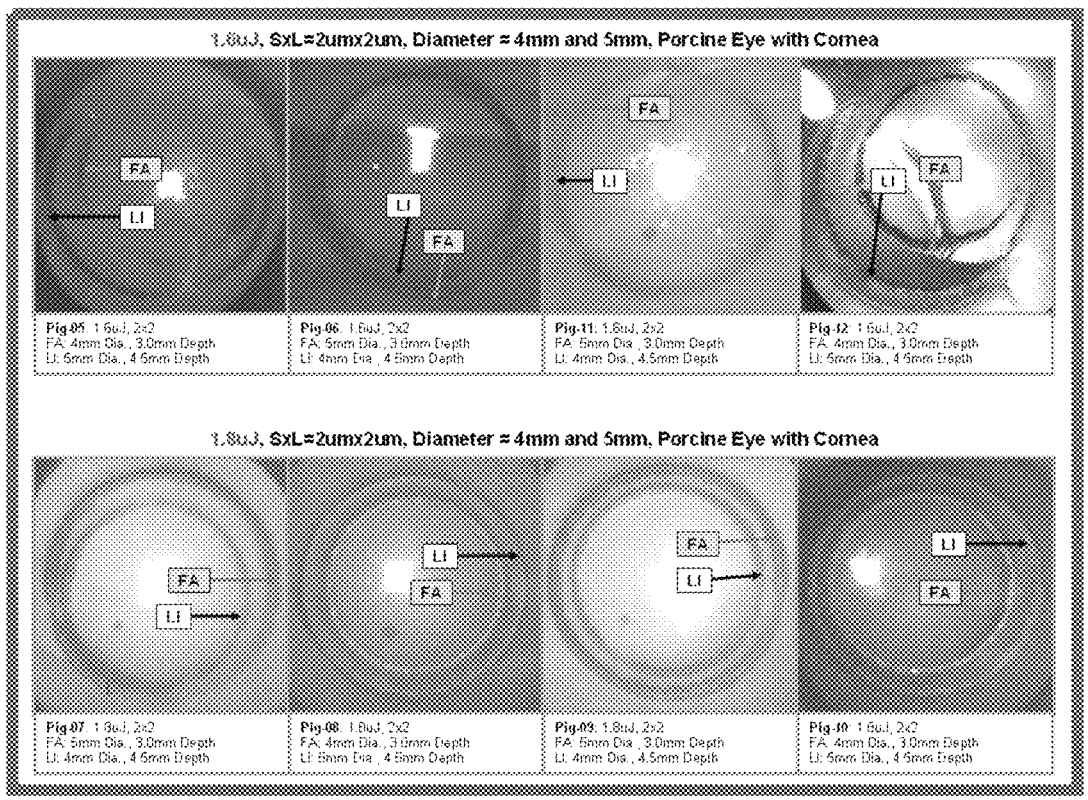
FIG. 17 illustrates a comparison of the effects of laser cutting in a lens of ex-vivo pig eyes docked with a liquid patient interface (LI) and a flat applanating patient interface (FA) according to one embodiment of the present invention.

A comparison of the effects of laser cutting in the lens of ex-vivo pig eyes docked with a liquid PI (LI) and flat applanating PI (FA) are shown in FIG. 17. At 1.6 µJ, the liquid PI (LI) may yield stronger tissue effects than the flat applanating PI (FA). At 1.8 µJ, the liquid PI (LI) and the flat applanating PI (FA) may both produce strong tissue effects at the full circumference. Since the liquid PI (LI) typically requires lower cut energy, it was selected for the clinical study.

In regards to retina safety, ANSI, ICE, and ICNIRP require the same or similar Maximum Permissible Exposures (MPE) in the retinal hazard region for lasers. The most restrictive one of the three MPEs (i.e., MPE for single pulse, MPE for average power, and MPE for grouped pulse) must be met. These MPEs are determined by wavelength, pulse duration, NA of the beam, pulse repetition frequency, and the exposure time. The irradiance at the retina produced by the laser depends on pulse energy, pulse repetition frequency, NA of the beam, the focus location, and the structure of eye. The studies conducted demonstrated that the peak irradiance of the modified optical system at the retina is well below the most restrictive ANSI MPE for grouped pulse.

The above described field upgrade unit and studies demonstrate the feasibility of adapting a pre-existing laser optical system, such as a femtosecond laser corneal workstations, to perform laser capsulotomy. As described herein adapting a pre-existing laser optical system may involve implementing the described range finder, zoom beam expander (ZBX), and/or a novel use of an existing patient interface (PI) to form a liquid interface. The performance of the modified or upgraded systems may include one or more of the following: locating the anterior lens capsule by the range finder within ±20 µm in depth; extending the laser focal range to about 0 mm to 7 mm by using ZBX—a range that is sufficient to cover the capsulotomy needs for approximately 99% of cataractous eyes; setting the diameter for laser capsulotomy to any value within about 6.5 mm; ensuring that all three ANSI MPE limits are met; ensuring that the upgraded systems provide equivalent performance in flap creation mode compared with existing the corneal workstations; and the like.

A femtosecond laser capsulotomy clinical trial was conducted using the above described systems and methods for 19 cataract patients. The human clinical trials validated the laser cut time at between about 12~40 seconds. The upgrades described herein may be implemented via field service at moderate costs.

While the disclosure has been described in connection with specific embodiments thereof, it will be understood that it is capable of further modifications. This application is intended to cover many variations, uses, or adaptations of the disclosure following, in general, the disclosed principles and including such departures from the disclosure as come within known or customary practice within the art to which the disclosure pertains and as may be applied to the essential features hereinbefore set forth.

What is claimed is:

1. A system for treating an eye of a patient, the eye including a fluid and a tissue posterior to a cornea, the system comprising:
   a femtosecond laser configured for directing femtosecond energy pulses along an optical path;
   an optical system disposed along the optical path from the laser, the optical system including a focusing lens and a scanner so as to scan a non-plasma-generating focus of the femtosecond energy along a scan path within the patient's eye, the scan path extending posterior to the patient's cornea within the fluid and the tissue so that the scan path includes a first location disposed within the tissue of the eye and a second location disposed within the cornea;
   a sensor, comprising an image acquisition device, oriented and disposed along a part of the optical path outside of the patient's eye so as to sense a first signal to form a first reflectance image associated with a first focus location within the eye, and to sense a second signal to form a second reflectance image associated with a second focus location within the eye, the first and second signals being reflectance signals of the femtosecond pulses of the laser which have a wavelength equal to that of the femtosecond pulses, which are reflected respectively by the eye at the first and second focus locations; and
   a computing device communicatively coupled with the sensor, wherein the computing device determines a location of an interface between the fluid and the tissue of the eye based on a comparison between a size of a focal spot in the first reflectance image formed by the first signal and a size of a focal spot in the second reflectance image formed by the second signal.

2. The system of claim 1, wherein the non-plasma-generating focus of the femtosecond energy has an energy level less than a bubble formation threshold of the fluid or the tissue of the eye.

3. The system of claim 1, wherein the sensor is configured to sense a dimension of a spot size at the focus, and wherein the computing device is configured to determine if the beam spot size is indicative of wrinkling associated with engagement between the cornea and a corneal-shaping patient interface of the system.

4. The system of claim 1, wherein the computing device is configured to determine and transmit pachymetry data for the eye.

5. The system of claim 1, wherein the computing device is configured to determine a separation between a posterior capsule and a retina of the eye.

6. The system of claim 1, wherein the computing device is configured to determine a curvature of a patient interface contact surface of the system.

7. The system of claim 1, wherein the computing device is configured to detect bubbles at a meniscus between a patient interface contact surface of the system and the eye.

8. The system of claim 1, wherein the computing device is configured to determine a location of an apex or vertex of a contact surface of a patient interface of the system.

* * * * *